United States Patent
De Cerqueira Leite et al.

(10) Patent No.: US 9,512,186 B2
(45) Date of Patent: Dec. 6, 2016

(54) RECOMBINANT STRAIN OF MYCOBACTERIUM BOVIS BACILLUS CALMETTE-GUERIN (BCG), IMMUNOGENIC COMPOSITION AND USE

(71) Applicant: FUNDACAO BUTANTAN, Sao Paulo, SP (BR)

(72) Inventors: Luciana Cezar De Cerqueira Leite, Sao Paulo (BR); Ivan Pereira Nascimento, Sao Paulo (BR)

(73) Assignee: Fundação Butantan, Avenida Vital (BR)

( * ) Notice: Subject to any disclaimer, the term of this patent is extended or adjusted under 35 U.S.C. 154(b) by 0 days.

(21) Appl. No.: 14/379,149

(22) PCT Filed: Feb. 18, 2013

(86) PCT No.: PCT/BR2013/000049
§ 371 (c)(1),
(2) Date: Aug. 15, 2014

(87) PCT Pub. No.: WO2013/120159
PCT Pub. Date: Aug. 22, 2013

(65) Prior Publication Data
US 2015/0152145 A1 Jun. 4, 2015

(30) Foreign Application Priority Data
Feb. 17, 2012 (BR) .................. 10 20120003790

(51) Int. Cl.
A61K 39/04 (2006.01)
A61K 49/00 (2006.01)
A61K 39/02 (2006.01)
C07K 14/245 (2006.01)
A61K 39/00 (2006.01)

(52) U.S. Cl.
CPC ............. C07K 14/245 (2013.01); A61K 39/04 (2013.01); *A61K 2039/523* (2013.01); *A61K 2039/55516* (2013.01)

(58) Field of Classification Search
CPC .... A61K 39/00; A61K 39/02; A61K 39/0258; A61K 39/04
USPC .................. 424/9.1, 9.2, 184.1, 234.1, 248.1
See application file for complete search history.

(56) References Cited

FOREIGN PATENT DOCUMENTS

WO    WO2004/108154    * 12/2004

OTHER PUBLICATIONS

Miyaji, E.N., et al. Infection and Immunity. vol. 69, No. 2, pp. 869-874, Feb. 2001.*

* cited by examiner

*Primary Examiner* — Rodney P Swartz
(74) *Attorney, Agent, or Firm* — Finnegan, Henderson, Farabow, Garrett & Dunner, L.L.P.

(57) ABSTRACT

The present invention relates to recombinant *Mycobacterium* strain that encodes the mutated *Escherichia coli* LT heat-labile toxin or the A subunit of the mutated *Escherichia coli* LT heat-labile toxin. The present invention also relates to strains of *Mycobacterium* that encode the LT heat-labile toxin or the A subunit of the LT heat-labile toxin of *Escherichia coli* mutated in position 63. Specifically, the present invention relates to strains of *Mycobacterium* that encode the LT heat-labile toxin or the A subunit of the LT heat-labile toxin of *Escherichia coli* mutated in position 63 from serine to lysine. The present invention also provides immunogenic compositions that comprise the strains of the present invention. The present invention further provides for the use of said strains and immunological compositions in the production of a vaccine for preventing tuberculosis and infections caused by *Mycobacterium tuberculosis*. Lastly, the present invention relates to methods for preventing or treating tuberculosis in animals.

20 Claims, 7 Drawing Sheets

ND STRAIN OF
RECOMBINANT STRAIN OF MYCOBACTERIUM BOVIS BACILLUS CALMETTE-GUERIN (BCG), IMMUNOGENIC COMPOSITION AND USE

SEQUENCE LISTING

The instant application contains a Sequence Listing which has been submitted electronically in ASCII format and is hereby incorporated by reference in its entirety. Said ASCII copy, created on Feb. 29, 2016, is named 12775.0001_SL.txt and is 33,087 bytes in size.

The present invention refers to recombinant *Mycobacterium* strains that encode the mutant *Escherichia coli* heat-labile toxin LT or the A subunit of the mutant *Escherichia coli* heat-labile toxin This invention also refers to strains of *Mycobacterium* that encode the mutant heat-labile toxin LT or the A subunit of the heat-labile toxin LT of *Escherichia coli* in position 63.

Specifically, this invention refers to strains of *Mycobacterium* that encode the mutant heat-labile toxin LT or the A subunit of the heat-labile toxin LT of *Escherichia coli* from serine to lysine at position 63.

This invention also provides immunogenic compositions that include the strains of the present invention.

This invention also provides for the use of the above mentioned strains and immunological compositions in the production of a vaccine for prevention against *tuberculosis* and infections caused by *Mycobacterium tuberculosis*.

Finally, the present invention refers to methods for preventing or treating *tuberculosis* in animals.

GROUNDS OF THE INVENTION

Mycobacteria

Mycobacteria compose the genus *Mycobacterium* of the family Mycobacteriacae of the order Actinomycetales of the class Actinomycetes. The mycobacteria that form this genus are shaped like slightly curved rods, measuring from 1 to 10 μm in length and 0.2 to 0.6 μm in diameter. These bacteria cannot be classified as either Gram-positive or Gram-negative. The most striking feature of this *bacillus* is the complex nature of its cell envelope, containing a relatively high percentage of lipids, which include the long chains of mycolic acid. This envelope confers strong hydrophobicity, making it resistant to lysis and relatively impermeable to antibiotics and other chemical agents. The bacilli are labeled acid-alcohol resistant, i.e., they are resistant to discoloration caused by weak acids after staining with Fuchsine or similar dyes. The genomic DNA contains a high content of guanosine/cytosine, between 58-79%, which impairs the use of the bacterium *Escherichia coli* as a genetic host. These aspects are considered basic characteristics for identifying the *bacillus* as a member of the genus *Mycobacterium* [ORME, I. (1995) Medical Intelligent Unit: Immunity to Mycobacteria, Austin: R. G. Lands Company, p. 5; JAWETZ, S. MELNICK, J. L. ADELBERG, E. A. (1995) Medical Microbiology. 21$^{st}$ Ed. Appleton & Lange, Stamford, Conn.; SHINNICK, T. M. & GOOD, R. C. (1994) Mycobacterial taxonomy. Eur J Clin Microbiol Infect M Dis 11: 884-901].

Mycobacteria have been classified in two main groups: slow-growing bacteria, which have a generation time of around 13 hours and can take from 3 weeks to 3 months of culturing to provide visible colonies; and the fast-growing bacteria, which have a generation time of around 2-5 hours. The slow-growing mycobacteria include many of the greatest animal and human pathogens, such as *M. tuberculosis*, *M. bovis*, *M. paratuberculosis*, *M. avium*, *M. leprae*, etc., while the fast-growing ones include non pathogenic species, such as *M. smegmatis*, *M. aurum*, *M. vaccae*, etc. Four of the five pathogenic species of mycobacteria are grouped in the *M. tuberculosis* complex—a group of four species that can cause the disease tuberculosis (*M. tuberculosis*, *M. bovis*, *Mycobacterium microtti* and *M. africanum*); the fifth is *M. leprae*, the agent that causes Hansen's disease (informally known as leprosy) [SHINNICK, T. M. & GOOD, R. C. (1994) Mycobacterial taxonomy. Eur J Clin Microbiol Infect Dis 11: 804-901; ORME, I. (1995) Medical Intelligent Unit: Immunity to Mycobacteria. Austin: R. G. Lands Company, p. 5; CONNELL, N. D. (2001) Expression systems for use in Actinomycetes and related organisms. *Current Opinion in Biotechnology* 12: 446-449].

*M. tuberculosis* (MTB) is transmitted primarily through the respiratory tract and although it can cause diseases in several organs, pulmonary *tuberculosis* is the most common. It is estimated that a third of the world population is infected with the *bacillus* and that 200 million will present symptoms of *tuberculosis*, of whom 35 million may die by 2020 if control and prevention measures are not taken (WHO Annual Publication, 2000).

Prophylaxis of *Tuberculosis* and Use of *Bacillus* Calmette-Guérin (BCG)

At the beginning of the last century, Albert Calmette and Camille Guérin attenuated a virulent strain of *Mycobacterium bovis*. This strain is currently known as *Bacillus* Calmette-Guérin (BCG), and is the only *tuberculosis* vaccine currently used successfully, having already been administered to more than three billion individuals worldwide.

Nevertheless, its efficacy against the adult form of *tuberculosis* has given rise to controversy, as it can range from 0-80%, depending on the study [Andersen, P. and Doherty, T. M. (2005) The success and failure of BCG—implications for a novel *tuberculosis* vaccine. Nat Rev Microbiol. 3: 656-662].

Hence, several efforts have been undertaken in the development of new vaccines, based on a) recombinant proteins or dominant MTB antigens; b) the expression of these antigens in various vectors, such as viral vectors, bacterial vectors or recombinant BCG-based vectors; c) other mycobacteria that do not cause *tuberculosis* such as *Mycobacterium smegmatis*; or d) the actual attenuated *M. tuberculosis* [Sweeney, K. A, Dao, G. M., Goldberg, P. F., Hsu, T., Venkataswamy, M. M., Henao-Tamayo, M., Ordway, D., Sellers, R. S., Jain, P., Chen, B., Chen, M., Kim, J., Lukose, R., Chan, J., Orme, I. M., Porcelli, S. A. and Jacobs, W. R Jr. (2011) A recombinant *Mycobacterium smegmatis* induces potent bactericidal immunity against *Mycobacterium tuberculosis*. Nat Med. 4:1261-1268; Kaufmann, S. H. (2010) Future vaccination strategies against *tuberculosis*: thinking outside the box. Immunity 33: 567-577.

In general, the idea behind these vaccines is to seek a way of imitating what happens in a real situation, i.e., to present the entire pathogen in dead or live form, yet attenuated and that does not provoke infection [Kaufmann, S. H. (2010) Future vaccination strategies against *tuberculosis*: thinking outside the box. *Immunity* 33: 567-577], or using another species of the same genus, also dead or attenuated, such as BCG, which has important antigens in common with the pathogen of interest. Another variant of these vaccines would be their use as live vehicles for presentation or expression of heterologous antigens, in this case MTB molecules being expressed in BCG or *M. smegmatis* [Sweeney, K. A, Dao, D. N., Goldberg, M. F., Hsu, T., Venkataswamy, M. M., Henao-Tamayo, M., Ordway, D., Sellers, R. S., Jain, P., Chen, B., Chen, M., Kim, J., Lukose, R., Chan, J., Orme, I. M., Porcelli, S. A. and Jacobs, W. R Jr. (2011) A recombinant *Mycobacterium smegmatis* induces potent bactericidal immunity against *Mycobacterium tuberculosis*. Nat Med. 41261-1268; Kaufmann, S. H. (2010) Future vaccination strategies against *tuberculosis*: thinking outside the box. Immunity 33: 567-577].

Despite efforts, the results in an animal model, when compared with the BCG vaccine, suggest a reduction in the bacillary load in the lungs of only 1.0 log, although following an immunization system based on prime-boost. In this immunization schedule, the first dose is administered using one of the above mentioned formulations followed by a second dose in another formulation, i.e., two immunizations with different formulations or presentations are required to achieve a better result than the BCG vaccine used at present, which is administered as a single dose [Sweeney, K. A, Dao, D. N., Goldberg, M. F., Hsu, T., Venkataswamy, M. M., Henao-Tamayo, M., Ordway, D., Sellers, R. S., Jain, P., Chen, B., Chen, M., Kim, J., Lukose, R., Chan, J., Orme, I. M., Porcelli, S. A. and Jacobs, W. R Jr. (2011) A recombinant *Mycobacterium smegmatis* induces potent bactericidal immunity against *Mycobacterium tuberculosis*. Nat Med. 4:1261-1268; Kaufmann, S. H. (2010) Future vaccination strategies against *tuberculosis*: thinking outside the box. Immunity 33: 567-577].

Recombinant BCG

BCG is the most widely used vaccine in the world as it has a long-lasting immune response and a very low frequency of serious adverse effects. This and other characteristics make BCG an excellent candidate as a vehicle for presentation of heterologous antigens through BCG-based recombinant vaccines (U.S. Pat. No. 6,673,353). In this regard, the expression of immunogenic domains of bacteria, viruses and parasites has been used successfully in BCG, generating recombinant strains (rBCG), which produce an immune response not only against the tubercle *bacillus*, but also against the pathogens whose proteins would be expressed in this rBCG (U.S. Pat. No. 5,504,005). However, it is worth emphasizing that in the rBCGs described to date, the addition of a heterologous immunogenic domain confers the expected specific immunological protection against the pathogens whose proteins would be expressed in the aforesaid rBCG. Reactions differing from those known habitually, i.e., in which rBCG confers different immunological protection from that expected, have not yet been described.

*Escherichia Coli* Heat-Labile Toxin LT and its Immunomodulator Properties

Adjuvant properties have been attributed to several bacterial toxins. For example, it is widely known that the tetanus (TT), diphtheria (DT) and cholera (CT) toxins as well as the *Escherichia coli* (*E. coli*) heat-labile toxin (LT) act as adjuvants that direct the immune response to Th2 when coadministered with other antigens [Ryan, E. J. et al. (2000) Modulation of innate and acquired immune responses by *Escherichia coli* heat-labile toxin: distinct pro and anti-inflammatory effects of the nontoxic AB complex and the enzyme activity. *J Immunol.* 165:5750-5759; Miyaji, E. N. et al. (2001) Induction of neutralizing antibodies against diphtheria toxin by priming with recombinant *Mycobacterium bovis* BCG expressing CRM197, a mutant diphtheria toxin. *Infect Immun.* 69:869-874].

In particular, the *E. coli* LT toxin is among the most potent adjuvants described so far [Lycke, N. et al. (199 The adjuvant effect of *Vibrio cholerae* and *Escherichia coli* heat-labile enterotoxins is linked to their ADP-ribosyltransferase activity. *Eur J Immunol.* 22: 2277-2281; Pizza, M. et al. (2001) Mucosal vaccines: nontoxic derivatives of LT and CT as mucosal adjuvants. *Vaccine,* 19:2534-2541].

The *E. coli* LT toxin is formed by a single A subunit molecule (LTA, 27 kDa) (SEQ ID NO: 11), with ADP-ribosyltransferase activity, bound to a B subunit pentamer (LTB, 11.6 kDa each (SEQ ID NO: 9) which binds to the ganlioside GM1 receptor of mammal cells. The LT-B subunit is a potent signaling molecule able to modulate the immune response. The immune-stimulatory effect of LTB appears to be related to its ability to increase the presentation of antigen via the class I (MHC-I) and class II (MHC-II) major histocompatibility complex, among other factors. The adjuvant effect of LTB, in turn, has been directly related to the activity of binding to GM1, through the activation of B cells and $CD4^+$ T cells by means of the interaction of the B subunit pentamers and GM1 receptors of these cells. Moreover, LTB increases antigen presentation through the activation of dendritic cells (DCs) and other antigen-presenting cells (APCs). The LTB binding to ganglioside GM1 allows the toxic A subunit to enter the cell [Spangler, B. D. (1992) Structure and function of cholera toxin, and the related *Escherichia coli* heat-labile enterotoxin. Microbiol Rev. 56: 622-647].

The use of LT as an adjuvant is not recommended due to the toxicity of the A subunit. As the B subunit is not toxic, it has been used more frequently as an adjuvant [de Haan, L., Verweij, W. R., Feil, I. K., Holtrop, M., Hol, W. G., Agsteribbe, E. and Wilschut, J. (1998) Role of GM1 binding in the mucosal immunogenicity and adjuvant activity of the *Escherichia coli* heat-labile enterotoxin and its B subunit. *Immunology,* 94: 424-430].

The immunomodulatory properties that lead to the increase in the immunogenicity and protective efficacy of LT have been widely studied. Although the mechanisms that lead to this effect are not well characterized, some aspects such as the increase in inflammatory cytokines and production of chemokines, as well as transient recruitment of effector cells of the immune system to the site of inflammation have been established as important factors. LT can also influence dendritic cell maturation, antigen presentation and T-cell activation, besides promoting the induction of response by antigen-specific cytotoxic T-cells in animal model. The use of LT as an adjuvant commonly leads to a balance of cytokines, involving the production of a response by cytokines with both Th1 and Th2 characteristics and some antibody classes in mice and humans.

This toxin is able to activate an immune response against another antigen when they are presented simultaneously on mucosal surface or by oral, intranasal or parenteral administration [Holmgren, J., Lycke, N. and Czerkinsky, C. (1993) Cholera toxin and cholera B subunit as oral-mucosal adjuvant and antigen vector systems. Vaccine, 11: 1179-1184].

As a consequence of these properties, LT has been employed extensively as an adjuvant in animal models. However, in spite of the immunomodulatory action of LT, this substance is highly toxic and inappropriate for clinical use in humans. Thus to avoid the toxicity associated with the use of the native toxin, while maintaining its adjuvant properties, different strategies have been used which include the isolation of the B subunit (nontoxic) and the construction of nontoxic mutants of LT, containing specific site-directed mutations. Using computational modeling studies of the structure of the LT protein, we have been able to identify some amino acids potentially involved in the enzymatic activity of this protein, which could be studied through their exchange by site-directed mutation [Magagnoli, O. et al., (1996) Infect Immun. 64: 5434-5438]. Some of these mutants, such as LTR192G (substitution of glycine for arginine at position 192), have mutation in a handle region that is protease-sensitive, making this region insensitive to the action of proteases, an essential, stage for the activation of enzymatic activity and consequently of its toxicity. Other mutants exhibit a mutation in the enzymatically active region of the A subunit, such as LTR72 (substitution of arginine for alanine at position 72), which retains only 1% of the ADP-ribosyltransferase activity.

Another important mutant is LTK63 (substitution of lysine for serine at position 63). This mutation eliminates the ADP-ribosyltransferase activity associated with toxicity while eliminating the latter. However, it maintains all the other biological properties, including adjuvant properties of the native LT [Pizza, M., et al., (2001) Mucosal vaccines: nontoxic derivatives of LT and CT as mucosal adjuvants. Vaccine, 19:2534-2541].

LTK63 has been shown to act as a potent adjuvant when administered parenterally or through the mucosa. De Haan and collaborators [De Haan, L., Holtrop, M., Verweij, W. R., Agsteribbe, E. and Wilschut, J. (1999) Mucosal immunogenicity and adjuvant activity of the recombinant A subunit of the Escherichia coli heat-labile enterotoxin. Immunology, 97: 706-7013] suggest that adjuvants using nontoxic LTA in association with the LTB pentamer may be more potent than adjuvants using the B subunit alone, as the complex could stimulate the immune system more strongly than each molecule individually. Data that indicate an important function of the A subunit enzymatically inactive in the induction of an immune response, as well as in immunomodulatory activities, such as effects on antigen processing and presentation, support this view.

Expression of LT and its Variants

Recombinant LTB (SEQ ID NO: 9) and LTK63 (SEQ ID NO: 8) have been expressed typically in E. coli. However, other expression systems have been used. The LTB molecule was expressed in Mycocabtrium bovis BCG, Lactobacillus casei, Saccharomyces cerevisiae, Pichia pastoris, and plants that: include Oryza sativa (rice), Lactuca sativa (lettuce) and Peperomia pellucid. LTK63 has also been expressed in tobacco and chloroplasts, as well as attenuated Salmonella enterica serovar Typhimurium [da Hora, V. P. et al. (2011) Non-toxic derivatives of LT as potent adjuvants. Vaccine, 29: 1538-15441.

However, the goal of all these studies was to use the LT molecule or one of its subunits or variants to produce vaccines against E. coli. The use of LT in tuberculosis vaccines was not described or suggested in the existing literature.

OBJECTIVES OF THE INVENTION

One objective of this invention is to provide recombinant Mycobacterium strains that encode the mutant Escherichia coli heat-labile toxin LT or the A subunit of the mutant Escherichia coli heat-labile toxin LT In particular, one of the goals of this invention is to provide recombinant strains of Mycobacterium bovis Bacillus Calmette Guerin (BCG), which encode the mutant Escherichia coli heat-labile toxin LT or the A subunit of the mutant Escherichia coli heat-labile toxin LT More specifically, one of the goals of this invention is to provide strains of Mycobacterium, in particular Mycobacterium bovis Bacillus Calmette Guerin (BCG), which encode the mutant Escherichia coli heat-labile toxin LT or A subunit at position 63.

More specifically, one of the goals of this invention is to provide strains of Mycobacterium, in particular Mycobacterium bovis Bacillus Calmette Guerin (BCG), which encode the mutant Escherichia coli heat-labile toxin LT or A subunit at position 63 from serine to lysine, respectively rBCG-LTK63 and rBCG-LTAK63.

The present invention is also aimed at providing immunogenic compositions that involve the strains of this invention.

Another objective of the invention is to provide the use of the above mentioned strains and immunological compositions in the production of vaccines for prevention against tuberculosis and/or infections caused by Mycobacterium tuberculosis or by other mycobacteria.

In particular, the present invention has the objective of providing improved BCG vaccines against tuberculosis (i.e. that induce better protection than the conventional BCG strain) which involve the recombinant strains of Mycobacterium bovis Bacillus Calmette Guerin (BCG) of this invention.

This invention is also designed to provide methods for preventing or treating tuberculosis in animals, more particularly humans.

DEFINITIONS

Abbreviations are used several times within the scope of this patent application. Their definitions as used in this request are summarized below:

BCG refers to attenuated Mycobacterium bovis, Bacillus Calmette-Guérin;

LTK63 refers to Escherichia coli heat-labile toxin containing the A subunit modified by site-directed mutagenesis.

LTAK63 (SEQ ID NO: 8) refers to the A subunit of the Escherichia coli heat-labile toxin, modified by site-directed mutagenesis; and rBCG-LTK63 (SEQ ID NO: 1) or rBCG-LTAK63 (SEQ ID NO: 2) refers to the recombinant BCG expressing LTK63 (SEQ ID NO: 10) or LTAK63 (SEQ ID NO:7), respectively.

DESCRIPTION OF THE FIGURES

The figures below are part of this report and are included here to illustrate certain aspects of the invention. The purpose of the invention can be better understood with reference to one or more of these figures, in combination with the detailed description of the modality of choice presented here.

DETAILED DESCRIPTION OF THE INVENTION

Description of the Strains

Figure 1:
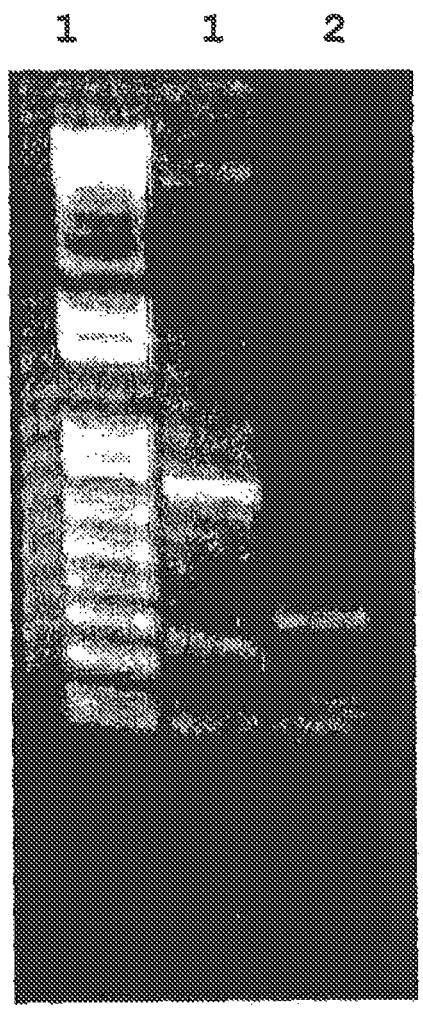
FIG. 1 shows an agarose gel containing the PCR products that confirm the presence of the LTK63 gene in the recombinant BCG (rBCG-LTK63). The PCR products were amplified from plasmid DNA extracted from the rBCG-LTK63 construction using specific initiator oligonucleotides to amplify the LTA subunit or the LTB unit. 1 Kb plus, molecular weight; well 1, complete LTA fragment (~700 bp); well 2, complete LTB fragment (~316 bp).
Figure 2:
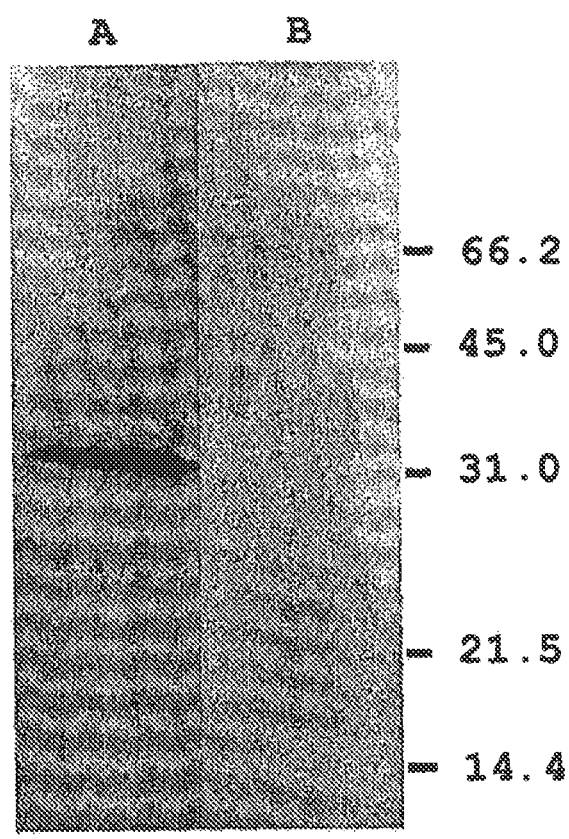
FIG. 2 shows the characterization of the LTAK63 expression (~31.0 kDa) in recombinant BCG. Extract of soluble proteins (~10 μg) of rBCG transformed with pLNIP-LTAK63 (A), or empty BCG as negative control (B) were used in this immunoassay. Anti-LT 1:1000 (polyclonal) rabbit serum was used.
Figure 3:
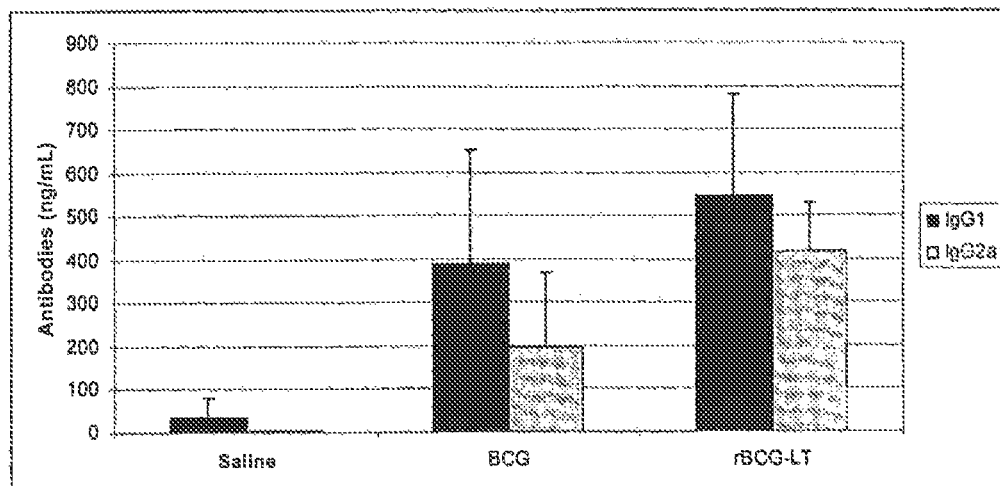
FIGS. 3 and 4 show the comparative analysis of the response of antibodies IgG1 and IgG2a induced against proteins recovered from the BCG culture supernatant—PDS Female BALB/c mice aged four weeks (18-22 g), from the Animal Facility of the School of Veterinary Medicine—USP (São Paulo University), were immunized with BCG or rBCG-LT (FIG. 3) or with BCG or rBCG-LTAK63 (FIG. 4) and the isotypes determined in isolated sera one day before the MTB challenge or 90 days after immunization. The sera of 5 animals per group were analyzed individually by ELISA, using specific mice anti IgG1 and IgG2a antibodies.
Figure 4:
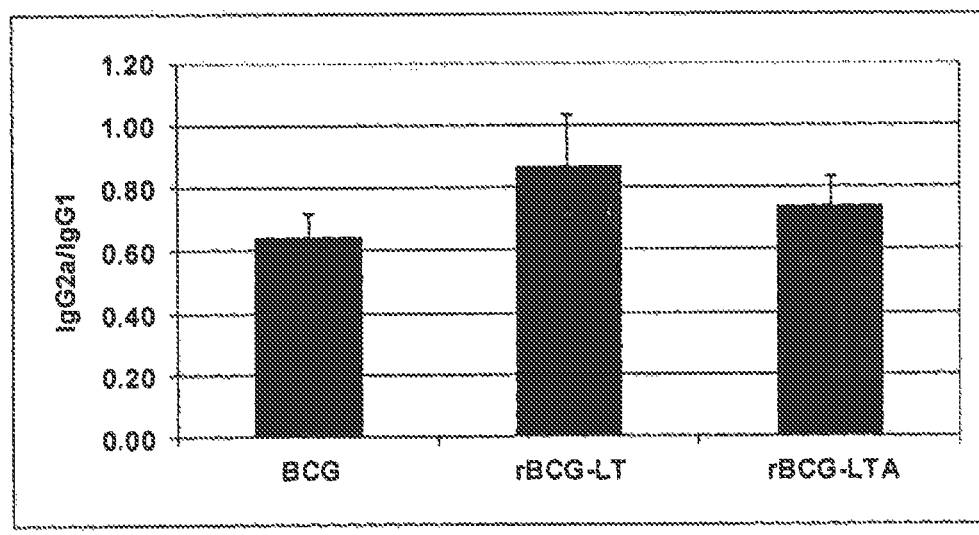
Figure 5:
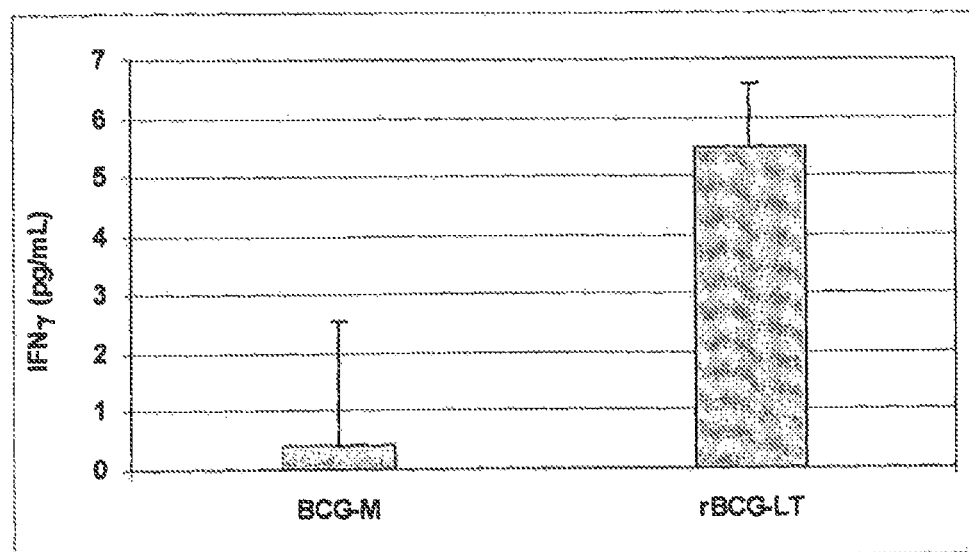
FIGS. 5 and 6 show the production of IFN-γ by splenocytes cultivated in the presence of PDS. Female BALB/c mice were immunized with $1 \times 10^6$ CFU of BCG or rBGC-LT (FIG. 5) or BCG, or rBCG-LTAK63 (FIG. 6) and after four weeks or eight weeks, respectively, the spleens were recovered and single-cell preparations were cultivated in vitro ($2 \times 10$ cells/well) in the presence of 2.0 µg/mL of PDS. The supernatants of the cultures were recovered after 48 h and the levels of IFN-γ determined by ELISA.
Figure 6:
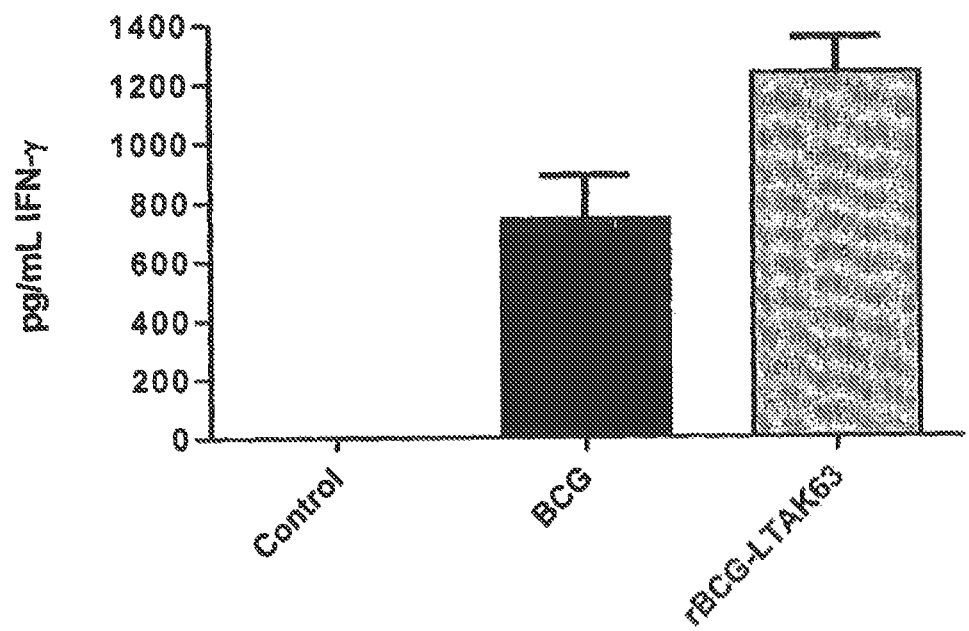

The present invention refers to recombinant strains of *Mycobacterium* that encode the mutant *Escherichia coli* heat-labile toxin LT This invention also refers to recombinant strains of *Mycobacterium* that encode the A subunit of the mutant *Escherichia coli* heat-labile toxin LT.

In particular, this invention refers to strains of *Mycobacterium* that encode the mutant heat-labile toxin LT or A subunit of the *Escherichia coli* heat-labile toxin LT at position 63.

More particularly, this invention refers to strains of *Mycobacterium* that encode the mutant heat-labile toxin LT or A subunit of the *Escherichia coli* heat-labile toxin at position 63 from serine to lysine, respectively rBCG-LTK63 and rBCG-LTAK63.

The above mentioned mutations allow the *Escherichia coli* heat-labile toxin LT or the A subunit of the *Escherichia coli* heat-labile toxin LT encoded by *Mycobacterium* to maintain the adjuvant properties of the native LT, yet they lose the ADP-ribosyltransferase activity associated with toxicity, thus avoiding toxicity problems in the case of humans or other animals.

Strains of *Mycobacterium* that encode the heat-labile toxin LT or the A subunit of the *Escherichia coli* heat-labile toxin LT that exhibit other mutations in their sequence that target an equivalent effect, i.e. maintenance of the adjuvant properties of the native LT and reduction or suppression of toxicity, are also involved in this invention. Such mutations may include, but are not limited to, positions 72 and 192.

The strains of this invention are obtained from any strain of the genus *Mycobacterium* as carrier for presentation of one or more antigens of different organisms, obtained and cloned in expression vector in mycobacteria and inserted by means genetic manipulation.

The recombinant *Mycobacterium* strains of this invention preferably include strains of the MTB complex, *Mycobacterium tuberculosis, Mycobacterium bovis, Mycobacterium microtti* and *Mycobacterium africanum* or of fast-growing mycobacteria, *Mycobacterium smegmatis, M. aurum, M. vaccae*, etc.

The recombinant *Mycobacterium* strains of this invention more preferably include strains of *Mycobacterium bovis* Bacillus Calmette Guerin (BCG).

Description of the Immunogenic Compositions

The present invention refers to immunogenic compositions involving one or more strains of this invention and one or more within a physiologically acceptable vehicle, excipient, diluent or solvent.

The compositions of this invention preferably include strains of *Mycobacterium bovis* Bacillus Calmette Guerin (BCG), which encode the mutant heat-labile toxin LT at position 63 from serine to lysine, i.e., rBCG-LTK63.

Alternatively, the compositions of this invention preferably include strains of *Mycobacterium bovis* Bacillus Calmette Guerin (BCG), which encode the A subunit of the mutant heat-labile toxin LT at position 63 from serine to lysine, i.e., rBCG-LTAK63.

The compositions of this invention may also involve a mixture of strains of *Mycobacterium bovis* Bacillus Calmette Guerin (BCG), which encode the mutant heat-labile toxin LT at position 63 from serine to lysine, i.e., rBCG-LTK63 and the A subunit of the mutant heat-labile toxin LT at position 63 from serine to lysine, i.e., rBCG-LTAK63.

The immunogenic compositions of this invention may also additionally involve one or more antigens, preferably inactivated toxins. Such antigens may be for use in the prevention and/or treatment of *tuberculosis* or of other diseases caused by different pathogens. The inactivated components of the synergic immunogenic compositions of this invention can be obtained using any method known in the technique, such as chemical procedures, such as treatment with formaldehyde or hydrogen peroxide, or even DNA recombination techniques.

According to this invention, adjuvants are attenuated or dead molecules, components, macromolecules or microorganisms that potentiate the response to immunizations, reduce the amount of antigen required and direct the type of immune response to be developed, besides sustaining it for a longer period of time, as an immunogen; it is any material or substance that alters the type, speed, intensity or duration of the immune response.

The compositions of this invention can also include excipients, such as bactericides, bacteriostatics, antioxidants, preservatives, buffers, stabilizers, pH adjusters, osmolarity adjusters, antifoaming agents and surfactants; and residues of antigen inactivation or fractionating agents, growth media components and solvents commonly used in the production of vaccines; examples of these types of component can be found in the *Epidemiology and Prevention of Vaccine-Preventable Diseases The Pink Book*, 11th edition, under "*Vaccine Excipient & Media Summary*" (Centers for Disease Control and Prevention. Epidemiology and Prevention of Vaccine-Preventable Diseases. Atkinson W, Wolfe S, Hamborsky J, McIntyre L, eds. 11th ed. Washington, D.C.: Public Health Foundation, 2009) incorporated here as a reference.

As employed in this invention, the use of the term "pharmaceutically acceptable" means an inert nontoxic solid, semisolid liquid excipient, diluent, ancillary formulation of any kind, or simply a sterile aqueous medium, such as saline solution. Some examples of the materials that can serve as pharmaceutically acceptable vehicles are sugars, such as lactose, glucose and sucrose, the searches, such as corn starch and potato starch, cellulose and its derivatives, such as sodium carboxymethyl cellulose, ethylcellulose and cellulose acetate, cyclodextrin; oils, such as peanut oil, cottonseed oil, sunflower oil, sesame oil, olive oil, corn oil and soybean oil; glycols, such as propylene glycol, poly oils, such as glyceringlycol, sorbitol, mannitol and polyethylene; esters, such as ethyl laurate, ethyl oleate, agar; buffering agents, such as aluminum hydroxide and magnesium hydroxide; alginic acid; pyrogen-free water; isotonic saline, Ringer's solution; buffer solutions of ethyl alcohol and phosphate, as well as other compatible nontoxic substances used in pharmaceutical formulations.

A range of routes for administration of the immunotherapy compositions and vaccines described in this invention is available. The particular method selected will depend on the particular active ingredient selected, the necessary dosage for therapeutic efficacy and on the patient to whom the composition is to be administered. The methods of the present invention can generally be practiced using any biologically acceptable means of administration, i.e., any method that produces effective levels of immune response without causing clinically undesirable adverse effects. Such methods of administration include the intradermal, oral, rectal, sublingual, topical, nasal, transdermal or parenteral routes. The term "parenteral" includes subcutaneous, intravenous, epidural, irrigation, intramuscular, release or infusion pumps. In this invention particularly, the intradermal, oral, parenteral and nasal routes are preferred for administering the compositions advocated here.

For parenteral administration, the active ingredients can be dissolved in a pharmaceutical vehicle and administered as a solution, or emulsion, including micro- and nanoemulsions, or suspension. Examples of appropriate vehicles are water, saline, dextrose solutions, fructose solutions or oils of animal, vegetable or synthetic origin.

For nasal administration, the active ingredients can be dissolved in a pharmaceutical vehicle and administered as a solution, or emulsion, including micro- and nanoemulsions, or suspension. Examples of appropriate vehicles are water and saline solution or solid suspensions, such as spray, lactose, fructose or chitosan flakes. Other vehicles can also contain other ingredients, e.g., preservatives, suspensor agents, solubilizing agents, buffers and alike.

The immunogenic compositions of this invention are preferably for intradermal, oral and parenteral administration.

Properties of the Strains and of the Immunogenic Compositions of this Invention

The strains and the immunogenic compositions of this invention exhibit an unexpected synergic effect on the immune response against *Mycobacterium*. The recombinant antigens of LTK63 or LTAK63 exhibit the unexpected technical effect of inducing an adjuvant effect against the proteins of the actual *Mycobacterium*.

As can be seen in the examples below, the strains and the immunogenic compositions of this invention exhibit the unexpected technical effect of producing a more intense anti-TB immune response than vaccines involving traditional BCG. In other words, the addition of an immunogenic domain, such as the nontoxic subunit LTAK63 of the *E. coli* heat-labile toxin, which is known to have no bond with any type of mycobacteria, in a recombinant *mycobacterium*, in particular BCG, brings about an increase in the protective response against *tuberculosis*.

In particular the strains and the immunogenic compositions of this invention promote a decrease in the bacillary load in the lungs in animal models of *tuberculosis*.

Moreover, the strains and the immunogenic compositions of this invention lead to a significant increase in the expression of IFN-γ in relation to the control group, a cytokine considered essential in the response against *tuberculosis*; this fact indicates a Th1 polarized response.

The strains and immunogenic compositions of this invention also lead to a significant increase in TNF-α. Since TNF-α is related as a signaler of proinflammatory action, characterizing the acute phase of the inflammatory process triggered by the bacilli, then the vaccines of this invention promote direct activation of the immune system.

Finally, we can conclude that the strains and the immunogenic compositions of this invention, in combining mycobacteria, in particular BCG, and toxin derivatives of other pathogens, preferably of *Escherichia coli*, generating a recombinant mycobacterial strain, constitute a new vaccine that is more potent and effective than conventional BCG for prophylaxis or immunization against *tuberculosis*.

Use of the Strains and of the Immunogenic Compositions of this Invention.

Considering the properties of the recombinant strains of *Mycobacterium* and of the immunogenic compositions of this invention, another aspect of this invention is the use of immunogenic compositions to prevent infections caused by mycobacteria, in particular *Mycobacterium tuberculosis* in animals, more particularly humans.

Another aspect of this invention is the use of one or more recombinant strains of *Mycobacterium* or of one or more immunogenic compositions of this invention in the production of a vaccine.

More particularly, an aspect of this invention is the use of one or more Recombinant *Mycobacterium* strain or of one or more immunogenic compositions of this invention in the production of a vaccine for the prevention and/or treatment of *tuberculosis* and/or infections caused by mycobacteria.

Yet another aspect of this invention is the methods used to prevent or treat *tuberculosis* in animals, more particularly humans.

EXAMPLES

To allow a better understanding of this invention and to clearly demonstrate the technical advances obtained, we present below, as examples, the results of the different assays carried out in relation to this invention.

In Example 1 we describe the obtainment of the vaccines of this invention. The other examples (2 to 3) serve to illustrate the properties and the use or the vaccine of this invention. These examples are presented merely for illustration and should in no way be considered as limiting the scope and sphere of this invention.

Example 1

Obtainment of the rBCG-LTK63 and rBCG-LTAK63 Vaccines

This example describes the obtainment of the rBCG-LTK63 and rBGC-LTAK63 vaccines.

a) Preparation of competent BCG stock batch: to prepare stocks of competent BCG, one or more BCG colonies were cultured in Middlebrook 7H9 plus Tween-80 liquid medium and supplemented with 10% albumin dextrose catalase (MB7H9/Tw/ADC) until the exponential phase. Composition of the Middlebrook 7H9 medium according to the manufacturer (Difco-ED) Ammonium Sulfate, L-Glutanic Acid, Sodium Citrate, Pyridoxine, Biotin, Disodium Phosphate, Mono-Potassium Phosphate, Ferric Ammonium Citrate, Magnesium Sulfate, Calcium Chloride, Zinc Sulfate and Copper Sulfate. After this the culture was sedimented by centrifugation at 4000 rpm and washed twice with 10% glycerol at 4° C., then finally resuspended in 5% of the original volume, with 10% glycerol and stored at −70° C. until its transformation by electroporation with pNL12-LTK63 plasmid or with pNL12-LTAK63 plasmid.

b) Construction of the expression vector of the LTK63 gene in recombinant BCG here called pNL12-LTK63: the mycobacterial expression vector used for expression of LTK63 in recombinant BCG is called pMIP12 and was described by Le Dantec [Le Dantec et al. 2001 J Bacteriol. 183: 2157-2164]. The LTK63 gene was kindly contributed by Dr. Rino Rappuoli (Novartis). The expression vector in recombinant BCG of the LTK63 gene was constructed using conventional molecular biology methods. The LTK63 gene was amplified by PCR using the following initiator oligonucleotides: N-terminus

```
                                           (SEQ ID NO: 3)
        (5'-TAGGGTACCCAAAAATATAACTTCATTTTTTTTATTTT-3'
``` containing the Kpn I restriction site (underlined) and C-terminus

```
                                           (SEQ ID NO: 4)
          (5'-TAGCTGCAGCTAGTTTTTCATACTGATTGCCC-3',
``` containing the Pst I restriction site (underlined). The PCR product corresponding to the LTK63 gene was generated using the following PCR conditions: 94° C. for 4 minutes; 25 cycles of 94° C. for 1 min, 50° C. for 1 min and 72° C. for 30 s; and 4° C. final. This PCR product was then digested with the restriction enzymes Kpn I and Pst I and then cloned in the expression vector pMIP12, which was also previously digested with the same enzymes Kpn I and Pst I, thus generating the expression vector called pMIP12/LTK63.

Gene Sequence of Plasmid pNP12-LTK63 (SEQ ID NO: 1)

```
Gene sequence of plasmid pNP12-LTK63 (SEQ ID NO: 1)
GCGCCCAATACGCAAACCGCCTCTCCCCGCGCGTTGGCCGATTCATTAATGCAGCTGGCACGACAGGTTTCCCGACTGGAA AGCGGGCAGTGAGCGCAACGCAATTAATGTGAGTTAGCTCACTCATTAGGCACCCCAGGCTTTACACTTTATGCTTCCGGC TCGTATGTTGTGTGGAATTGTGAGCGGATAACAATTTCACACAGGAAACAGCTATGACCATGATTACGAATTCGAGCTCGA CTTAATTAACTCCGGGTGGTCACTGAGTACATCCCGTCGGTGCGTTCGGCATCGGTCGGGGTGTGGGTGGGTGTCGGCTCC CGCGACGAAGGACGAAGCGTCGCGGGTGCCGCCCACTTCTTGGAGCATCTGCTGTTCAAGGCCACCCCGACGCGCACGCGG TCGACATCGCGCAGGCTGTCGATGCCGTCGGCGGTGAGCTGAACGCGTTCACCACGCGCGAGCACACCTGTTACTACGCGC ATGTGCTCGACTCCGACCTGGAGCTCGCGGTCGACCTGGTGCGCCGATGTCGTGTTGCGTGGGCGTTGTGCCACCGAGGAT GTCGAAGTGGAGCGCGACGTCGTCCTCGAGGAGATCGCCATGCGTGACGACGATCCCGAGGACAGCCTCGGCGACGTGTTC CTCTCGGCGATGTTCGGCGATCACCCGGTGGGACGTCCGGTGATCGGCAGCGTCGAGTCGATCGAGACCATGACGCGTGCA CAGCTGCATTCGTTCCACGTCCGGCGTTACACACCCGAACGGATGATCGTGGCGGTGGCCGGCAACGTCGACCACGACGTG TGGTGTCGTTGGTCCGAGAGCATTTCGGCCCCCGGCTGGAGGCCGACGTTCCGCGGTGGCTCCCCGTAAGGCTCGGGACGG GTCGGTGGTAAGCCATCGCTGCTCGTGGTCGACCGCGACGGGGAACAGTCCCATGTCTCGCTGGGCGTTCGCACGCCCGGC CGGCACTGGGAGCACCGGTGGGCCCTGTCGGTGTTGAACACCGCGCTGGGAGGCGGGCTCAGTTCTCGTCTGTTCCAACAG

ATTCGCGAGTCCCGCGGCCTGGCCTACCTCGGTGTACTCGACCGTGACCACTTCGCGACAGCGGGGCTCTGTCGGTGTAT

GCGGGATGTCAGCCGGAACGTTTCGACGAAGTGGTGCGGGTGACCACCGAAGTTTTGGAAGGTGTTGCCAGAGACGGGATC

ACCGCCGACGAATGCCGGATCGCCAAAGGCTCGTTGCGCGGTGGGCTGGTGCTCGGCCTGGAGGATTCCGGATCACGTATG

CACCGGATCGGCCGTAGCGAGCTCAATTACGGTGgAGCACCGGACCATCGACCACACGCTGGCCCAGATCGAGGCAGTCAC
```

-continued

```
TCTAGAAGAGGTCAACGCCGTCGCTCACCAGTTGCTGTCGCGGGACTACGGTGCCGCCGTACTCGGTCCCTATAGTTCGAA
AAAGGCGCTGCCACAACAGCTTCAAACTATCGCCGGCTGACCCGCTACACTGGGTCCAATGGATTAGAAGGAGAAGTACCG
ATGGGATCCGGTACCAATGGCGACAGATTATACCGTGCTGACTCTAGACCCCCAGATGAAATAAAACGTTCCGGAGGTCTT
ATGCCCAGAGGGCATAATGAGTACTTCGATAGAGGAACTCAAATGAATATTAATCTTTATGATCACGCGAGAGGAACACAA
ACCGGCTTTGTCAGATATGATGACGGATATGTTTCCACTAAGCTTAGTTTGAGAAGTGCTCACTTAGCAGGACAGTCTATA
TTATCAGGATATTCCACTTACTATATATATGTTATAGCGACAGCACCAAATATGTTTAATGTTAATGATGTATTAGGCGTA
TACAGCCCTCACCCATATGAACAGGAGGTTTCTGCGTTAGGTGGAATACCATATTCTCAGATATATGGATGGTATCGTGTT
AATTTTGGTGTGATTGATGAACGATTACATCGTAACAGGGAATATAGAGACCGGTATTACAGAAATCTGAATATAGCTCCG
GCAGAGGATGGTTACAGATTAGCAGGTTTCCCACCGGATCACCAAGCTTGGAGAGAAGAACCCTGGATTCATCATGCACCA
CAAGGTTGTGGAAATTCATCAAGAACAATCACAGGTGATACTTGTAATGAGGAGACCCAGAATCTGAGCACAATATATCTC
AGGGAATATCAATCAAAAGTTAAGAGGCAGATATTTTCAGACTATCAGTCAGAGGTTGACATATATAACAGAATTCGGGAT
GAATTATGAGGATTAGGAGAAGTACCGGAATTCATGAATAAAGTAAAATGTTATGTTTTATTTACGGCGTTACTATCCTCT
CTATGTGCATACGGAGCTCCCCAGTCTATTACAGAACTATGTTCGGAATATCGCAACACACAAATATATACGATAAATGAC
AAGATACTATCATATCGGAATCGATGGCAGGCAAAAGAGAAATGGTTATCATTACATTTAAGAGCGGCGCAACATTTCAG
GTCGAAGTCCCGGGCAGTCAACATATAGACTCCCAAAAAAAAGCCATTGAAAGGATGAAGGACACATTAAGAATCACATAT
CTGACCGAGACCAAAATTGATAAATTATGTGTATGGAATAATAAAACCCCCAATTCAATTGCGGCAATCAGTATGGAAAAC
TAGCTGCAGCATCACCATCACCATCACTAGTGAAATAGCGAAACACGGGATCGGGCGAGTTCGACCTTCCGTCGGTCTCGC
CCTATTAATAGTGGCATGCAAGCTTGGCACTGGCCGTCGTTTTACAACGTCGTGACTGGGAAAACCCTGGCGTTACCCAAC
TTAATCGCCTTGCAGCACATCCCCCTTTCGCCAGCTGGCGTAATAGCGAAGAGGCCCGCACCGATCGCCCTTCCCAACAGT
TGCGCAGCCTGAATGGCGAATGGCGCCTGATGCGGTATTTTCTCCTTACGCATCTGTGCGGTATTTCACACCGCATATGCA
GGGGGGGGGGGCGCTGAGGTCTGCCTCGTGAAGAAGGTGTTGCTGACTCATACCAGGAACGAGGACAGTCGCACGACGAA
GTTCTTCTGGATCGCGCCCGTGCTGGAAGCACTCAACCTCGAAGCGTGTGGTTGCGGAGCCATCTAGCAACCACACGAAAC
ATGCGCAACGAACCGCGCAACGAACAACGCCTAGAACTGGCCCTAGATGAGCTGACTCGTATCGTTGGTAAACCTAGTTTG
ACCAGCATGTTTTAACTACGTTCGGTGAGCTGTCAACGGGGCCTGTAACGGCACAACGAACCGTGCAACGAGAGTGGCCAC
GGATGCCACCACAGGCACTACAACGGAGTTCGCCACGTACATCACCACAACCACCGATTCTGGCGGTGAGCTCCCCGATAT
TCAGCGGAAATGGCTTGGTATCGACCAAGATTCGTAGAACCCCGTCTCGTCTGGCTGGTATTCAAAACGGGCGCAACGAAA
CACGCAACGAGACAGGCATGGCCCAAACCAGAAAACTAGCGTCTACCAGGACTTTTACCTGTCCGACCCGTTGCAACGGAA
CCCCCCACGGAACCCCCGCGACACCCGCTCCCCAATTGCGTTAGAACAGCGGTGGATTGTCGGCTTCGTTGTGGGCCTTTT
GAGCCGCTTCCTGTTCTGCCGCACGCTCTTTCCTCGCCCGATAGCCGAGTCGCTTAACGGTGTCCAGATGCAGCCCGAAAT
GTTTGGCCGTTTGCGGCCAAGAGTGGCCCTCGTCGTCGTGATAGGCGCGGATGCGTTCGCGGCGTGCAGCCTGCTCGGCGA
GCCACTCGCTGCGTTCCTGCGCCACGAGCCGGACGACGTGGCGTTCGGATAGTCCGGTGATTCGAGCGCCTTCGGCGGCGG
TCACGCGCCGCTTTTTGCGGACAGTCGGCTGCCGGTTGTAGCCGTCGCTGTAGCCGTCGCTCATAGCAATGCCTCCATGGC
TGACGCGGACTTTGCGCGCCGCGCAACTGTGCTCGCCGCCGTGCGCGCTGCTGCGCCCTTCCGCGAGATGGCCGACTGGCG
CGCACTGAGTGTGGCCTCGTAGACCACGATCCCGTCCGCCCAAATGCGCGACTTGGTTGTGATCCAACGCCAAATGCTGTT
GGCGATGGCGCGGACCTCGCTGTCCGGTAGCGGTCCGGGACACACGTCGTTGCACGGGAATTCGGCGTTTCGCGCGTGGCA
CTCGGCATAGATCGCGCGGCCGAGTCCGTCCACGTTCCGGGTCGGCAGGTAGATCCGCATGAGGGCGGGACGATAGGCCCA
CAACCTGACGGAATCGAACAGTGCGCAATTCCGCCCTAGCGGCGTCGGAGCCGCTTTGTACGTGGTCTGCTGACGCCAGCG
CGGCGGTGGCATGTTCGCGCCGAGCTCGGCCTCGATGTGGCTGAGTGTGTAGAGATCTGAGTGGAGCCATTCCGTTTCCCA
GGCGATGTGGCCGGGGTTTTTGGTCATGAGGCCTGAGTAACTGCGGTCGCCGTCGACGGCGCGCCGAAGGCCTTCGGCGCA
CGCCGCCATGTATGCGAGCGGCTTACGCCGCGCGTATTCGGTGCGTGGAACAGGGGCGTTGAGTGCCCACACTGCGTGTGC
```

-continued
```
GTGGCCGTTGGCGCGATTGCCCACGATCGCGTTGGGCAGCGGATGGGACCCCCGGGCGCTGAGCGCTCGGAGCGCTGCGTC
TGGATGGTCTACGTCCACGACCAGCAGGTTTGCCAGCGCTGTTGGGTTCGCCTCGATGTACCGGCGGCCTAGGGCCGACGC
GCGGCTTTGGCGGTAGATCCCCTCGAGCAGATCGTCGCTTGCCAGCGGCCAGTACGGCAGCCAGAGCTGCTCAAATTCGTC
GGCGACGTGGCTCACGCTTGGTAGTAGACCACGATTAATCACCGGTGTATGGTCCGACACGAGCTCCAAGTCAGATATTTC
GCTGAGGGGCCACCCCACAACTGCACACTCCCCCGCTCTCCCGTCGAGCCCTGGTGGTGGAACACCAGCGACAGCCGAGCA
CCCCCAACCACCTGTACCAACCAGGAGGAACACATGCGTCGTTTCGAGGACGTTTCCGGGCCGCTGAGAGCCGCTGTGGCG
GCCGTACACGCCGCCTTAGACCCGTTAGACCCCCTGCCGCCTGAATGCGCGGGTACGAGCCACACAGCGCCCGAACTTACG
GAGCTGGTGGGCTCACCTGGCTTTATGGCGTACGAATCGGCTGTGTGCGACCTGTTGGGCGAGGTGAGGTACGCGCTACTC
ACGCTGGCAAGGGCGACACAGCCGCCCCACCGAGCCCGCACGGCCGCGCGGTGTCAACAACCGGGTGAGTCGTGCACAC
CAGCAGGTGTTCGAGGCTTGGCTCGAAGTGCAGGACATCGTGGCGAACGCCGCCCGATGAGCCGCGCCTTACGCTGGCTGC
CAGCCGTTCGCGGGCTGGTTGGTGCAGCGCGTCGAGCGGTTAGAGGCCCTGCGGTGTTCCACCACCGCAGGGCCTCGCCCT
TTTTAAGGCTGAATTTGCTTGTCTCCGAATCCAACTGGCTTGTCCAAGGGTGTATCTACGCTTAATCCAAAGTTCAAACGA
GGGGATTACACATGACCAACTTCGATAACGTTCTCGGCTCGATCCTGAATCGCCCCATCATCCAGCCAGAAAGTGAGGGAG
CCACGGTTGATGAGAGCTTTGTTGTAGGTGGACCAGTTGGTGATTTTGAACTTTTGCTTTGCCACGGAACGGTCTGCGTTG
TCGGGAAGATGCGTGATCTGATCCTTCAACTCAGCAAAAGTTCGATTTATTCAACAAAGCCGCCGTCCCGTCAAGTCAGCG
TAATGCTCTGCCAGTGTTACAACCAATTAACCAATTCTGATTAGAAAAACTCATCGAGCATCAAATGAAACTGCAATTTAT
TCATATCAGGATTATCAATACCATATTTTTGAAAAAGCCGTTTCTGTAATGAAGGAGAAAACTCACCGAGGCAGTTCCATA
GGATGGCAAGATCCTGGTATCGGTCTGCGATTCCGACTCGTCCAACATCAATACAACCTATTAATTTCCCCTCGTCAAAAA
TAAGGTTATCAAGTGAGAAATCACCATGAGTGACGACTGAATCCGGTGAGAATGGCAAAAGCTTATGCATTTCTTTCCAGA
CTTGTTCAACAGGCCAGCCATTACGCTCGTCATCAAAATCACTCGCATCAACCAAACCGTTATTCATTCGTGATTGCGCCT
GAGCGAGACGAAATACGCGATCGCTGTTAAAAGGACAATTACAAACAGGAATCGAATGCAACCGGCGCAGGAACACTGCCA
GCGCATCAACAATATTTTCACCTGAATCAGGATATTCTTCTAATACCTGGAATGCTGTTTTCCCGGGGATCGCAGTGGTGA
GTAACCATGCATCATCAGGAGTACGGATAAAATGCTTGATGGTCGGAAGAGGCATAAATTCCGTCAGCCAGTTTAGTCTGA
CCATCTCATCTGTAACATCATTGGCAACGCTACCTTTGCCATGTTTCAGAAACAACTCTGGCGCATCGGGCTTCCCATACA
ATCGATAGATTGTCGCACCTGATTGCCCGACATTATCGCGAGCCCATTTATACCCATATAAATCAGCATCCATGTTGGAAT
TTAATCGCGGCCTCGAGCAAGACGTTTCCCGTTGAATATGGCTCATAACACCCCTTGTATTACTGTTTATGTAAGCAGACA
GTTTTATTGTTCATGATGATATATTTTTATCTTGTGCAATGTAACATCAGAGATTTTGAGACACAACGTGGCTTTCCCCCC
CCCCCCTATCATTGCAGCACTGGGGCCAGATGGTAAGCCCTCCCGTATCGTAGTTATCTACACGACGGGGAGTCAGGCAAC
TATGGATGAACGAAATAGACAGATCGCTGAGATAGGTGCCTCACTGATTAAGCATTGGTAACTGTCAGACCAAGTTTACTC
ATATATACTTTAGATTGATTTAAAACTTCATTTTTAATTTAAAAGGATCTAGGTGAAGATCCTTTTTGATAATCTCATGAC
CAAAATCCCTTAACGTGAGTTTTCGTTCCACTGAGCGTCAGACCCCGTAGAAAAGATCAAAGGATCTTCTTGAGATCCTTT
TTTTCTGCGCGTAATCTGCTGCTTGCAAACAAAAAAACCACCGCTACCAGCGGTGGTTTGTTTGCCGGATCAAGAGCTACC
AACTCTTTTTCCGAAGGTAACTGGCTTCAGCAGAGCGCAGATACCAAATACTGTCCTTCTAGTGTAGCCGTAGTTAGGCCA
CCACTTCAAGAACTCTGTAGCACCGCCTACATACCTCGCTCTGCTAATCCTGTTACCAGTGGCTGCTGCCAGTGGCGATAA
GTCGTGTCTTACCGGGTTGGACTCAAGACGATAGTTACCGGATAAGGCGCAGCGGTCGGGCTGAACGGGGGGTTCGTGCAC
ACAGCCCAGCTTGGAGCGAACGACCTACACCGAACTGAGATACCTACAGCGTGAGCTATGAGAAAGCGCCACGCTTCCCGA
AGGGAGAAAGGCGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGCTCGTCAGGGGGCGGAG
CCTATGGAAAAACGCCAGCAACGCGGCCTTTTTACGGTTCCTGGCCTTTTGCTGGCCTTTTGCTCACATGTTCTTTCCTGC
GTTATCCCCTGATTCTGTGGATAACCGTATTACCGCCTTTGAGTGAGCTGATACCGCTCGCCGCAGCCGAACGACCGAGCG
CAGCGAGTCAGTGAGCGAGGAAGCGGAAGA
``` c) Construction of the expression vector of the LTAK63 gene in recombinant BCG here called pLN12-LTAK63: the expression vector in recombinant BCG of the LTAK63 gene was constructed using conventional molecular biology methods. The LTAK63 gene was amplified by PCR from the LTK63 gene using the following initiator oligonucleotides: N-terminus (SEQ ID NO: 5)
(5'-TAGGGATCCAATGGCGACAGATTATACCGTTG-3'), containing the BamH I restriction site (underlined) and C-terminus (SEQ ID NO: 6)
(5'-TAGGGTACCTAATTCATCCCGAATTCTGTTATA-3')

containing the Kpn I restriction site (underlined). The PCR product corresponding to the LTAK63 gene was generated using following PCR conditions: 94° C. for 4 minutes; 25 cycles of 94° C. for 1 min, 50° C. for 1 min and 72° C. for 30 s; and 4° C. final. This PCR product was then digested with the restriction enzymes BamH I and Kpn I and then cloned in the expression vector pMIP12, which was also previously digested with the same enzymes BamH I and Kpn I, thus generating the expression vector called pLNIP/LTAK63.

Gene Sequence of Plasmid pNL12-LTAK63 (SEQ ID NO: 2)

```
Gene sequence of plasmid pNL12-LTAK63 (SEQ ID NO: 2)
GCGCCCAATACGCAAACCGCCTCTCCCCGCGCGTTGGCCGATTCATTAATGCAGCTGGCACGACAGGTTTCCCGACTGGA

AAGCGGGCAGTGAGCGCAACGCAATTAATGTGAGTTAGCTCACTCATTAGGCACCCCAGGCTTTACACTTTATGCTTCCG

GCTCGTATGTTGTGTGGAATTGTGAGCGGATAACAATTTCACACAGGAAACAGCTATGACCATGATTACGAATTCGAGCT

CGACTTAATTAACTCCGGGTGGTCACTGAGTACATCCCGTCGGTGCGTTCGGCATCGGTCGGGGTGTGGGTGGGTGTCGG

CTCCCGCGACGAAGGACGAAGCGTCGCGGGTGCCGCCCACTTCTTGGAGCATCTGCTGTTCAAGGCCACCCCGACGCGCA

CGCGGTCGACATCGCGCAGGCTGTCGATGCCGTCGGCGGTGAGCTGAACGCGTTCACCACGCGCGAGCACACCTGTTACT

ACGCGCATGTGCTCGACTCCGACCTGGAGCTCGCGGTCGACCTGGTGCGCCGATGTCGTGTTGCGTGGGCGTTGTGCCAC

CGAGGATGTCGAAGTGGAGCGCGACGTCGTCCTCGAGGAGATCGCCATGCGTGACGACGATCCCGAGGACAGCCTCGGCG

ACGTGTTCCTCTCGGCGATGTTCGGCGATCACCCGGTGGGACGTCCGGTGATCGGCAGCGTCGAGTCGATCGAGACCATG

ACGCGTGCACAGCTGCATTCGTTCCACGTCCGGCGTTACACACCCGAACGGATGATCGTGGCGGTGGCCGGCAACGTCGA

CCACGACGTGTGGTGTCGTTGGTCCGAGAGCATTTCGGCCCCCGGCTGGAGGCCGACGTTCCGCGGTGGCTCCCCGTAAG

GCTCGGGACGGGTCGGTGGTAAGCCATCGCTGCTCGTGGTCGACCGCGACGGGGAACAGTCCCATGTCTCGCTGGGCGTT

CGCACGCCCGGCCGGCACTGGGAGCACCGGTGGGCCCTGTCGGTGTTGAACACCGCGCTGGGAGGCGGGCTCAGTTCTCG

TCTGTTCCAACAGATTCGCGAGTCCCGCGGCCTGGCCTACCTCGGTGTACTCGACCGTGGACCACTTCGCGACAGCGGGG

CTCTGTCGGTGTATGCGGGATGTCAGCCGGAACGTTTCGACGAAGTGGTGCGGGTGACCACCGAAGTTTTGGAAGGTGTT

GCCAGAGACGGGATCACCGCCGACGAATGCCGGATCGCCAAAGGCTCGTTGCGCGGTGGGCTGGTGCTCGGCCTGGAGGA

TTCCGGATCACGTATGCACCGGATCGGCCGTAGCGAGCTCAATTACGGTGgAGCACCGGACCATCGACCACACGCTGGCC

CAGATCGAGGCAGTCACTCTAGAAGAGGTCAACGCCGTCGCTCACCAGTTGCTGTCGCGGGACTACGGTGCCGCCGTACT

CGGTCCCTATAGTTCGAAAAAGGCGCTGCCACAACAGCTTCAAACTATCGCCGGCTGACCCGCTACACTGGGTCCAATGG

ATTAGAAGGAGAAGTACCGATGGGATCCGGTACCAATGGCGACAGATTATACCGTGCTGACTCTAGACCCCCAGATGAAA

TAAAACGTTCCGGAGGTCTTATGCCCAGAGGGCATAATGAGTACTTCGATAGAGGAACTCAAATGAATATTAATCTTTAT

GATCACGCGAGAGGAACACAAACCGGCTTTGTCAGATATGATGACGGATATGTTTCCACTAAGCTTAGTTTGAGAAGTGC

TCACTTAGCAGGACAGTCTATATTATCAGGATATTCCACTTACTATATATATGTTATAGCGACAGCACCAAATATGTTTA

ATGTTAATGATGTATTAGGCGTATACAGCCCTCACCCATATGAACAGGAGGTTTCTGCGTTAGGTGGAATACCATATTCT

CAGATATATGGATGGTATCGTGTTAATTTTGGTGTGATTGATGAACGATTACATCGTAACAGGGAATATAGAGACCGGTA

TTACAGAAATCTGAATATAGCTCCGGCAGAGGATGGTTACAGATTAGCAGGTTTCCCACCGGATCACCAAGCTTGGAGAG

AAGAACCCTGGATTCATCATGCACCACAAGGTTGTGGAAATTCATCAAGAACAATCACAGGTGATACTTGTAATGAGGAG

ACCCAGAATCTGAGCACAATATATCTCAGGGAATATCAATCAAAAGTTAAGAGGCAGATATTTTCAGACTATCAGTCAGA

GGTTGACATATATAACAGAATTCGGGATGAATTATGACTGCAGCATCACCATCACCATCACTAGTGAAATAGCGAAACAC
```

-continued

GGGATCGGGCGAGTTCGACCTTCCGTCGGTCTCGCCCTATTAATAGTGGCATGCAAGCTTGGCACTGGCCGTCGTTTTAC
AACGTCGTGACTGGGAAAACCCTGGCGTTACCCAACTTAATCGCCTTGCAGCACATCCCCCTTTCGCCAGCTGGCGTAAT
AGCGAAGAGGCCCGCACCGATCGCCCTTCCCAACAGTTGCGCAGCCTGAATGGCGAATGGCGCCTGATGCGGTATTTTCT
CCTTACGCATCTGTGCGGTATTTCACACCGCATATGCAGGGGGGGGGGGGCGCTGAGGTCTGCCTCGTGAAGAAGGTGTT
GCTGACTCATACCAGGAACGAGGACAGTCGCACGACGAAGTTCTTCTGGATCGCGCCCGTGCTGGAAGCACTCAACCTCG
AAGCGTGTGGTTGCGGAGCCATCTAGCAACCACACGAAACATGCGCAACGAACCGCGCAACGAACAACGCCTAGAACTGG
CCCTAGATGAGCTGACTCGTATCGTTGGTAAACCTAGTTTGACCAGCATGTTTTAACTACGTTCGGTGAGCTGTCAACGG
GGCCTGTAACGGCACAACGAACCGTGCAACGAGAGTGGCCACGGATGCCACCACAGGCACTACAACGGAGTTCGCCACGT
ACATCACCACAACCACCGATTCTGGCGGTGAGCTCCCCGATATTCAGCGGAAATGGCTTGGTATCGACCAAGATTCGTAG
AACCCCGTCTCGTCTGGCTGGTATTCAAAACGGGCGCAACGAAACACGCAACGAGACAGGCATGGCCCAAACCAGAAAAC
TAGCGTCTACCAGGACTTTTACCTGTCCGACCCGTTGCAACGGAACCCCCCACGGAACCCCCGCGACACCCGCTCCCCAA
TTGCGTTAGAACAGCGGTGGATTGTCGGCTTCGTTGTGGGCCTTTTGAGCCGCTTCCTGTTCTGCCGCACGCTCTTTCCT
CGCCCGATAGCCGAGTCGCTTAACGGTGTCCAGATGCAGCCCGAAATGTTTGGCCGTTTGCGGCCAAGAGTGGCCCTCGT
CGTCGTGATAGGCGCGGATGCGTTCGCGGCGTGCAGCCTGCTCGGCGAGCCACTCGCTGCGTTCCTGCGCCACGAGCCGG
ACGACGTGGCGTTCGGATAGTCCGGTGATTCGAGCGCCTTCGGCGGCGGTCACGCGCCGCTTTTTGCGGACAGTCGGCTG
CCGGTTGTAGCCGTCGCTGTAGCCGTCGCTCATAGCAATGCCTCCATGGCTGACGCGGACTTTGCGCGCCGCGCAACTGT
GCTCGCCGCCGTGCGCGCTGCTGCGCCCTTCCGCGAGATGGCCGACTGGCGCGCACTGAGTGTGGCCTCGTAGACCACGA
TCCCGTCCGCCCAAATGCGCGACTTGGTTGTGATCCAACGCCAAATGCTGTTGGCGATGGCGCGGACCTCGCTGTCCGGT
AGCGGTCCGGGACACACGTCGTTGCACGGGAATTCGGCGTTTCGCGCGTGGCACTCGGCATAGATCGCGCGGCCGAGTCC
GTCCACGTTCCGGGTCGGCAGGTAGATCCGCATGAGGGCGGGACGATAGGCCCACAACCTGACGGAATCGAACAGTGCGC
AATTCCGCCCTAGCGGCGTCGGAGCCGCTTTGTACGTGGTCTGCTGACGCCAGCGCGGCGGTGGCATGTTCGCGCCGAGC
TCGGCCTCGATGTGGCTGAGTGTGTAGAGATCTGAGTGGAGCCATTCCGTTTCCCAGGCGATGTGGCCGGGGTTTTTGGT
CATGAGGCCTGAGTAACTGCGGTCGCCGTCGACGGCGCGCCGAAGGCCTTCGGCGCACGCCGCCATGTATGCGAGCGGCT
TACGCCGCGCGTATTCGGTGCGTGGAACAGGGGCGTTGAGTGCCCACACTGCGTGTGCGTGGCCGTTGGCGCGATTGCCC
ACGATCGCGTTGGGCAGCGGATGGGACCCCGGGCGCTGAGCGCTCGGAGCGCTGCGTCTGGATGGTCTACGTCCACGAC
CAGCAGGTTTGCCAGCGCTGTTGGGTTCGCCTCGATGTACCGGCGGCCTAGGGCCGACGCGCGGCTTTGGCGGTAGATCC
CCTCGAGCAGATCGTCGCTTGCCAGCGGCCAGTACGGCAGCCAGAGCTGCTCAAATTCGTCGGCGACGTGGCTCACGCTT
GGTAGTAGACCACGATTAATCACCGGTGTATGGTCCGACACGAGCTCCAAGTCAGATATTTCGCTGAGGGGCCACCCCAC
AACTGCACACTCCCCGCTCTCCCGTCGAGCCCTGGTGGTGGAACACCAGCGACAGCCGAGCACCCCCAACCACCTGTAC
CAACCAGGAGGAACACATGCGTCGTTTCGAGGACGTTTCCGGGCCGCTGAGAGCCGCTGTGGCGGCCGTACACGCCGCCT
TAGACCCGTTAGACCCCCTGCCGCCTGAATGCGCGGGTACGAGCCACACAGCGCCCGAACTTACGGAGCTGGTGGGCTCA
CCTGGCTTTATGGCGTACGAATCGGCTGTGTGCGACCTGTTGGGCGAGGTGAGGTACGCGCTACTCACGCTGGCAAGGGC
GACACAGCCGCCCCACCGAGCCCGCACGGCCGCGCGCGGTGTCAACAACGGGTGAGTCGTGCACACCAGCAGGTGTTCG
AGGCTTGGCTCGAAGTGCAGGACATCGTGGCGAACGCCGCCCGATGAGCCGCGCCTTACGCTGGCTGCCAGCCGTTCGCG
GGCTGGTTGGTGCAGCGCGTCGAGCGGTTAGAGGCCCTGCGGTGTTCCACCACCGCAGGGCCTCGCCCTTTTTAAGGCTG
AATTTGCTTGTCTCCGAATCCAACTGGCTTGTCCAAGGGTGTATCTACGCTTAATCCAAAGTTCAAACGAGGGGATTACA
CATGACCAACTTCGATAACGTTCTCGGCTCGATCCTGAATCGCCCCATCATCCAGCCAGAAAGTGAGGGAGCCACGGTTG
ATGAGAGCTTTGTTGTAGGTGGACCAGTTGGTGATTTTGAACTTTTGCTTTGCCACGGAACGGTCTGCGTTGTCGGGAAG
ATGCGTGATCTGATCCTTCAACTCAGCAAAAGTTCGATTTATTCAACAAAGCCGCCGTCCCGTCAAGTCAGCGTAATGCT
CTGCCAGTGTTACAACCAATTAACCAATTCTGATTAGAAAAACTCATCGAGCATCAAATGAAACTGCAATTTATTCATAT
CAGGATTATCAATACCATATTTTTGAAAAAGCCGTTTCTGTAATGAAGGAGAAAACTCACCGAGGCAGTTCCATAGGATG

-continued

```
GCAAGATCCTGGTATCGGTCTGCGATTCCGACTCGTCCAACATCAATACAACCTATTAATTTCCCCTCGTCAAAATAAG

GTTATCAAGTGAGAAATCACCATGAGTGACGACTGAATCCGGTGAGAATGGCAAAAGCTTATGCATTTCTTTCCAGACTT

GTTCAACAGGCCAGCCATTACGCTCGTCATCAAAATCACTCGCATCAACCAAACCGTTATTCATTCGTGATTGCGCCTGA

GCGAGACGAAATACGCGATCGCTGTTAAAAGGACAATTACAAACAGGAATCGAATGCAACCGGCGCAGGAACACTGCCAG

CGCATCAACAATATTTTCACCTGAATCAGGATATTCTTCTAATACCTGGAATGCTGTTTTCCCGGGGATCGCAGTGGTGA

GTAACCATGCATCATCAGGAGTACGGATAAAATGCTTGATGGTCGGAAGAGGCATAAATTCCGTCAGCCAGTTTAGTCTG

ACCATCTCATCTGTAACATCATTGGCAACGCTACCTTTGCCATGTTTCAGAAACAACTCTGGCGCATCGGGCTTCCCATA

CAATCGATAGATTGTCGCACCTGATTGCCCGACATTATCGCGAGCCCATTTATACCCATATAAATCAGCATCCATGTTGG

AATTTAATCGCGGCCTCGAGCAAGACGTTTCCCGTTGAATATGGCTCATAACACCCCTTGTATTACTGTTTATGTAAGCA

GACAGTTTTATTGTTCATGATGATATATTTTTATCTTGTGCAATGTAACATCAGAGATTTTGAGACACAACGTGGCTTTC

CCCCCCCCCCCTATCATTGCAGCACTGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGATTAAGCATTGGTAACTGTCAGACCAAG

TTTACTCATATATACTTTAGATTGATTTAAAACTTCATTTTTAATTTAAAAGGATCTAGGTGAAGATCCTTTTTGATAAT

CTCATGACCAAAATCCCTTAACGTGAGTTTTCGTTCCACTGAGCGTCAGACCCCGTAGAAAAGATCAAAGGATCTTCTTG

AGATCCTTTTTTTCTGCGCGTAATCTGCTGCTTGCAAACAAAAAAACCACCGCTACCAGCGGTGGTTTGTTTGCCGGATC

AAGAGCTACCAACTCTTTTTCCGAAGGTAACTGGCTTCAGCAGAGCGCAGATACCAAATACTGTCCTTCTAGTGTAGCCG

TAGTTAGGCCACCACTTCAAGAACTCTGTAGCACCGCCTACATACCTCGCTCTGCTAATCCTGTTACCAGTGGCTGCTGC

CAGTGGCGATAAGTCGTGTCTTACCGGGTTGGACTCAAGACGATAGTTACCGGATAAGGCGCAGCGGTCGGGCTGAACGG

GGGGTTCGTGCACACAGCCCAGCTTGGAGCGAACGACCTACACCGAACTGAGATACCTACAGCGTGAGCTATGAGAAAGC

GCCACGCTTCCCGAAGGGAGAAAGGCGGACAGGTATCCGGTAAGCGGCAGGGTCGGAACAGGAGAGCGCACGAGGGAGCT

TCCAGGGGGAAACGCCTGGTATCTTTATAGTCCTGTCGGGTTTCGCCACCTCTGACTTGAGCGTCGATTTTTGTGATGCT

CGTCAGGGGGCGGAGCCTATGGAAAAACGCCAGCAACGCGGCCTTTTTACGGTTCCTGGCCTTTTGCTGGCCTTTTGCT

CACATGTTCTTTCCTGCGTTATCCCCTGATTCTGTGGATAACCGTATTACCGCCTTTGAGTGAGCTGATACCGCTCGCCG

CAGCCGAACGACCGAGCGCAGCGAGTCAGTGAGCGAGGAAGCGGAAGA
``` e) Obtainment of the strain of recombinant BCG expressing LTK63, rBCG-LTK63 to prepare rBCG-LTK63, a stock aliquot of 50-200 μl of competent BCG was mixed with 0.1-1 μg of pNL12-LTK63, in 2 mm electroporation cuvettes and this was submitted to pulsations of 2.5 kV, 25 μF and 1000Ω, in an electroporation system (GenePulser, BioRad, Hemel Hempstead, UK). After electroporation, the content of the cuvettes was recovered in 2 mL of medium (MB7H9/Tw/ADC) without antibiotic and incubated at 37° C. for 20 h before being seeded in Middlebrook 7H10 (Difco) solid medium, supplemented with 10% oleic acid-albumin-dextrose-catalase (MB7H10/OADC) plus kanamycin (20 μg/mL) for selection of the transformants. Approximate composition of the Middlebrook 7H10 solid medium according to the manufacturer (Difco-BD): Ammonium Sulfate, Potassium Monophosphate, Potassium Biphosphate, Sodium Citrate, Magnesium Sulfate, Calcium Chloride, Zinc Sulfate, Copper Sulfate, L-Glutamic Acid, Ferric Ammonium Citrate, Pyridoxine Hydrochloride, Biotin, Malachite Green and Agar. The selected rBCG colonies were then transferred to 5 mL of liquid medium of MB7H9/Tw/ADC culture with kanamycin (20 μg/mL).

e) Obtainment of the strain of recombinant BCG expressing the A subunit LTAK63, rBCG-LTAK63: to prepare rBCG-LTAK63, a stock aliquot of 50-200 μl of competent BCG was mixed with 0.1-1 μg of pLN12-LTAK63, in 2 mm electroporation cuvettes and this was submitted to pulsations of 2.5 kV, 25 μF and 1000Ω, in an electroporation system (GenePulser, BioRad, Hemel Hempstead, UK). After electroporation, the content of the cuvettes was recovered in 2 mL of medium (MB7H9/Tw/ADC) without antibiotic and incubated at 37° C. for 20 h before being seeded in Middlebrook 7H10 solid medium (Difco) supplemented with 10% oleic acid-albumin-dextrose-catalase (MB7H10/OADC) plus kanamycin (20 μg/mL) for selection of the transformants. Approximate composition of the Middlebrook 7H10 solid medium according to the manufacturer (Difco-BD): Ammonium Sulfate, Potassium Monophosphate, Potassium Biphosphate, Sodium Citrate, Magnesium Sulfate, Calcium Chloride, Zinc Sulfate, Copper Sulfate, L-Glutamic Acid, Ferric Ammonium Citrate, Pyridoxine Hydrochloride, Biotin, Malachite Green and Agar. The selected rBCG colonies were then transferred to 5 mL of liquid medium of MB7H9/Tw/ADC culture with kanamycin (20 μg/mL).

g) Preparation of the batches of rBCG-LTK63 and rBCG-LTAK63: Next the clones of these two strains were expanded to 50 ml of ME7H9/Tw/ADC liquid medium or in any medium described for the culture of mycobacteria plus kanamycin (20 μg/mL). After 2-3 weeks, when the culture reaches $DO_{600}$ 0.6-0.8, the samples were centrifuged, washed twice with distilled $H_2O$, resuspended in 1 mL of 10% glycerol and aliquoted at a volume of 50 μl, then stored at −80° C., for subsequent use in the immunization assays.

h) Evaluation of the batches of rBCG-LTK63 and rBCG-LTAK63: the viability of the batches of rBCG-LTK63 and rBCG-LTAK63 was assessed by counting the number of colony-forming units (CPU). The CFU number was determined as follows: one or more aliquots of the batch frozen at were thawed and several successive dilutions ($1\times10^2$, $1\times10^4$, $1\times10^5$ and $1\times10^6$) performed. Then the $1\times10^5$ and $1\times10^6$ dilutions were cultured in MB7H10/OADC medium plus kanamycin (20 μg/mL) and incubated at 37° C. After 3-4 weeks the number of colonies on the plate is counted.

i) Characterization of the Expression of LTK63 in Recombinant BCG

As it was not possible to determine the expression of the LTK63 gene using the classic immunoassay method, the characterization of the LTK63 expression was performed indirectly by confirming the presence of the LTK63 gene in the plasmid inside the recombinant BGC. This characterization was performed through PCR assay using specific initiators, the same already described above and used to amplify and clone the LTK63 gene in the pMIP12 vector (FIG. 1).

j) Characterization of the LTAK63 Expression in Recombinant BCG

Figure 7:
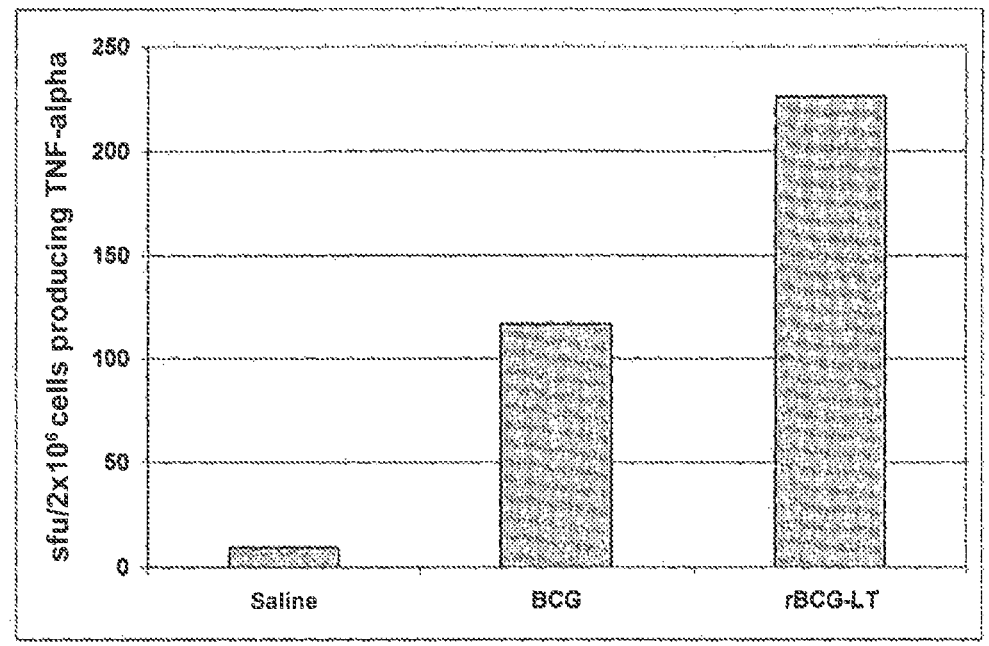
FIGS. 7 and 8 show the production of TNF-α by splenocytes cultivated in the presence of PDS. Female BALB/c mice were immunized with $1 \times 10^6$ CFU of BCG or rBGC-LT (FIG. 7) or BCG or rBCG-LTAK63 (FIG. 8). After 4 weeks (FIG. 7) or eight weeks (FIG. 8) the spleens were recovered and single-cell preparations were cultured in vitro ($2 \times 10^6$ cells/well) in the presence of 2.0 µg/mL of PDS. The culture supernatants were recovered after 24 h (FIG. 7) or 48 h (FIG. 9) and the TNF-α levels determined by ELISPOT (FIG. 7) or ELISA (FIG. 8, respectively). SFU=spot-forming units.
Figure 8:
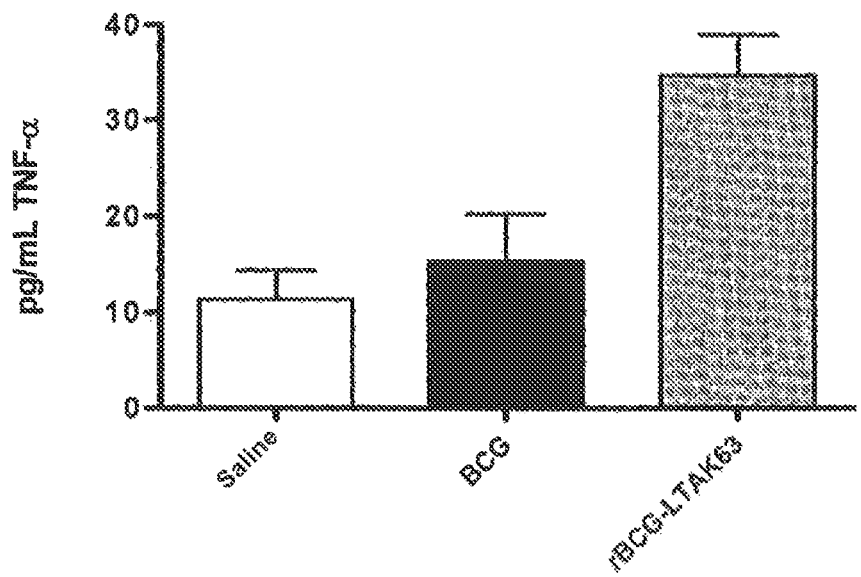
Figure 9:
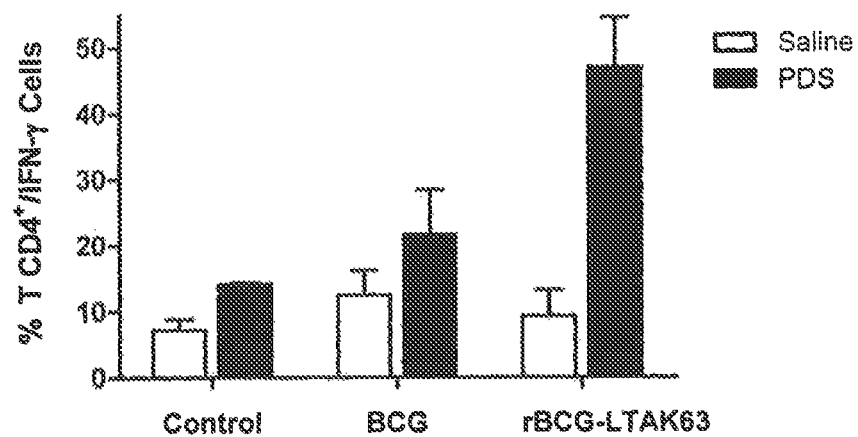
FIGS. 9 and 10 show the profile of CD4+ T cells that produce the cytokines TNF-γ and TNF-α, respectively. Female BALB/c mice (n=5 per group) were immunized by means of a single subcutaneous injection with $1 \times 10^6$ CFU/animal with BCG or rBCG-LTK63. A non-immunized group was used as negative control. Eight weeks after the immunization, the spleens were recovered and single-cell preparations were cultured in vitro ($2 \times 10^6$ cells/well) in the presence of 2.0 µg/mL of PDS. The profile of CD4+ T cells that produce the various cytokines were analyzed by Flow Cytometry (FACs) using specific anti-CD4, anti-INF-γ and anti-TNF-α antibodies marked with the appropriate fluorochrome.
Figure 10:
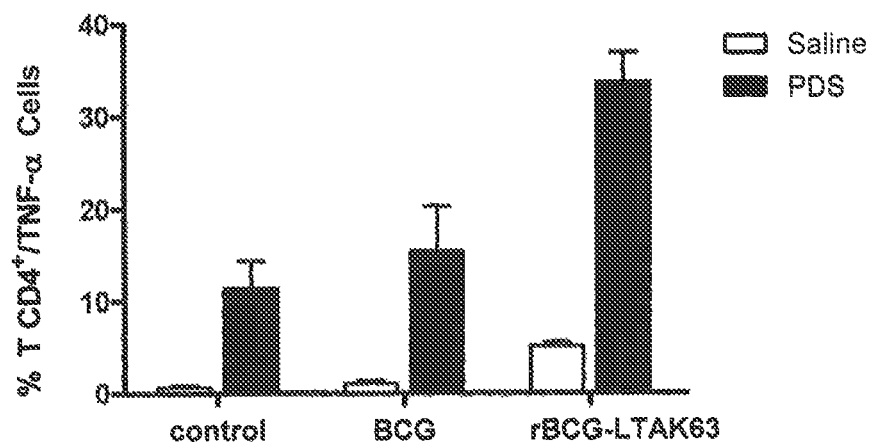

To verify the expression of the LTAK63 gene, the participants conducted an immunoassay (Western blot) using a polyclonal anti-LT serum and taking the following steps: one or more stock aliquots of rBCG-LTAK63 were sonicated for 1.5 min on ice at a constant amplitude corresponding to half the maximum value (Soniprep 150 MSE, UK) and centrifuged for precipitation of solids. The supernatants were recovered and the protein concentration dosed using the BIO-RAD Protein Assay (Bio-Rad) kit and employing bovine albumin as standard. Samples containing 10 μg of total proteins were applied in 10% polyacrylamide gel in presence of sodium dodecyl sulfate (SDS-PAGE 1.0%). Electrophoresis was performed at room temperature at 120 V until the dye reached the end of the gel. After electrophoresis, the proteins were transferred to PDVF membrane with 0.45 μm pores (GE Healthcare), using a semi-dry transfer system. The gel containing LT, as positive control, was glued on the PDVF membrane, immersed in transfer buffer (Tris 0.25 M Tris, pH 8.3, 0.129 M glycine and 20% methanol) and placed between five filter sheets also immersed in the same buffer. The set was placed between two plates and submitted to a current of 120 mA for 1.5 h at room temperature. At the end of the electrotransfer, the membrane was removed from the system and incubated in blocking solution (PBS containing 5% milk—milk/PBS) at 4° C. overnight. At the end of the blocking, the membrane was incubated at room temperature for 2 h with serum anti-LT diluted in milk/PBS (dilution 1:1000). After this incubation period, the PVDF membrane was washed three times under slight agitation, with 0.1% PBS/Tween20 (PBS-T) at 10-min intervals. The membrane was then incubated for 2 h under the same conditions in milk/PBS containing HRP-conjugated anti-IgG antibody (Sigma, Chem Co, St. Louis) and once again washed 3 times with PBS-T. The development was carried out by chemoluminescence using the ECL kit (Amersham) through exposure in a photo documentation apparatus (ImageQuant LAS4000—GE) (FIG. 2).

Example 2

Humoral and Cellular Immune Response Assay of Animals Immunized with rBCG-LTK63

The study subjects were adult female BALB/c mice (*Mus musculus*, Rodentia, Mammalia) aged 6-8 weeks originating from and maintained under the standard conditions of the Central Animal Facility of the School of Medicine of the University of São Paulo.

The animals were split into four groups (n=30):

BCG Group: animals immunized subcutaneously (s.c.) with 0.1 mL of BCG suspension ($1\times10^6$ CFU/mouse suspended in PBS 1×);

rBCG-LTK63 Group: animals immunized subcutaneously (s.c.) with 0.1 mL of rBCG-LTK63 suspension ($1\times10^6$ CFU/mouse suspended in PBS 1×);

rBCG-LTKA63 Group: animals immunized subcutaneously (s.c.) with 0.1 mL of rBCG-LTAK63 suspension ($1\times10^6$ CFU/mouse suspended in PBS 1×);

Control Group: animals inoculated with 0.1 mL of saline (PBS 1×).

a) Humoral response: for this procedure, the animals immunized or inoculated with the control, with BCG or rBCG-LT (FIG. 3) or with BCG or rBCG-LTAK63 (FIG. 4), underwent retro-orbital bleeding one day before the challenge and had their serum separated and aliquoted for subsequent characterization by the ELISA method. The isotypes were determined in serums isolated one day before the challenge against MTB or 90 days after immunization. The serums of 5 animals per group were analyzed individually by ELISA, using specific mouse anti IgG1 and IgG2a antibodies. The humoral response analysis was conducted comparing the concentration of the antibodies and/or specific subtypes IgG1 and IgG2a against PDS in the different immunization groups. The standard curve of these antibodies detected by specific monoclonal antibodies against the respective immunoglobulins was used for this purpose. The comparative analysis of the response of antibodies IgG1 and IgG2a induced against mycobacteria proteins (PDS) is important, as it can provide data on the profile or behavior of the immune response against these proteins. Emphasizing that a profile that shows a Th1-shifted response, and therefore more suitable for fighting an infection caused by MTB, can be identified through the IgG1/IgG2a ratio (FIGS. 3 and 4).

b) Cellular response of rBCG-LTK63: the evaluation of the cellular response of the Saline, BCG and rBCG-LTK63 groups was carried out using the ELISA and ELISPOT methods. Initially the spleens of the mice immunized as described above were removed 30 days after the first and only immunization, macerated and strained through screens with porosity of 70 μm (Cell strainer-BD Falcon, Bedford, Mass.). The splenocytes thus obtained from each group (Saline, BCG and rBCG-LTK63) were counted in a Neubauer chamber and had their viability assessed through Trypan blue staining. Cell dilution was then performed in RPMI complete medium [RPMI 1610 (GIBCO Life Technologies), penicillin (100 U/ml), streptomycin (100 μg/ml) plus 10% of bovine fetal serum], in the concentration of $2\times10^6$ cells/mL in the ELISA assay and $1\times10^5$ cells/mL in the ELISPOT assay, followed by seeding on a 24-well cell culture plate under PDS stimulus (2 μg/mL) and incubation for 24 hours and 48 hours, respectively, at 37° C. with 5% $CO_2$ atmosphere. In the group treated with rBCG-LTK63 a significant increase was observed in the levels of INF-γ and TNF-α in relation to the BCG Group. This fact indicates a Th1 polarized response (FIGS. 5 and 6).

c) Cellular response of rBCG-LTAK63 the evaluation of the cellular response of the Saline, BCG and rBCG-LTAK63 groups was carried out using the ELISA and Flow Cytometry (FACS) methods. Initially the spleens of the mice immunized as described above, were removed 60 days after the first and only immunization, macerated in Pyrex tissue homogenizers (Fischer Scientific—USA) and had the splenocytes recovered. The splenocytes thus obtained from each group (Saline, BCG and rBCG-LTAK63), were counted in a Neubauer chamber and had their viability assessed through Trypan blue staining. This stage was followed by cell dilution in RPMI complete medium [RPMI 1640 (GIBCO Life Technologies), penicillin (100 U/ml), streptomycin (100 μg/ml) plus 10% of bovine fetal serum], in the concentration of $2 \times 10^6$ cells/mL for the ELISA and FACS assays. In the ELISA assay the cells were seeded on a 24-well cell culture plate under PDS stimulus (2 μg/mL) and incubated for 48 hours, at 37° C. with 5% $CO_2$ atmosphere. In the FACS assay, a volume of 500 μL of cells was seeded on a 96-well plate under PDS stimulus (5 μg/mL) and incubated for 5 hours at 37° C. with 5% $CO_2$ atmosphere. Each sample was aliquoted and marked in three different tubes (200 μl/tube) following protocol of intracellular permeabilization and marking to separately analyze the intracellular expression of INF-γ and TNF-α within the subpopulation of $CD4^+$ T cells. A standard protocol provided by the manufacturer was used for the surface marking (anti-CD4-PerCP, BD Pharmingen, San Diego, Calif. USA) while the monoclonal (mAb) anti-IFN-γ (clone 4S.B3; ED Pharmingen, San Diego, Calif., USA) and anti-TNF-α (clone MAb11; BD Pharmingen, San Diego, Calif., USA) antibodies were used for intracellular marking. In the group treated with rBCG-LTAK63 a significant increase was observed in the levels of INF-γ and TNF-α in relation to the BCG group, both in the ELISA assays and in the flow cytometry assay. This fact indicates a Th1 polarized response (FIGS. 7 and 8, ELISA; FIGS. 9 and 10, FACS).

Example 3

Development of the Animal *Tuberculosis* Challenge Model—Assays of Protection Against an Intratracheal Challenge with the Strain of *Tuberculosis* H37Rv The study subjects were adult female C57BL/6 or BALB/c mice (*Mus musculus*, Rodentia, Mammalia) aged from 6 to 8 weeks and originating from and maintained under the standard conditions of the Central Animal Facility of the School of Medicine of the University of São Paulo.

The strain of *Mycobacterium tuberculosis* (MTB) 37HRv was used for the challenge assays. This strain was cultured in MB7H9/Tw/ADC liquid medium in an oven at 37° C. and 5% $CO_2$. The bacillary suspension of MTB was cultured in MB7B9/Tw/ADC medium for two weeks and only suspensions with at least 80% of viable bacilli were used for the challenge by the intratracheal route. The bacillary culture was centrifuged at 4000 rpm and washed twice with an equal volume of the culture with PBS 1×. Then the sediment was resuspended in 1 mL of PBS 1× and the number of bacilli estimated using the Macfarland scale.

The intratracheal challenge followed the method previously described [Pelizon et al. (2010) Neonatal BUG immunization followed by DNAhsp65 boosters: highly immunogenic but not protective against Rodentia *tuberculosis*—a paradoxical effect of the vector? Scand J Immunol. 71: 63-69. The mice were infected with $1 \times 10^5$ CPU of viable MTB or inoculated with 100 μl of PBS (Phosphate Buffered Saline) via intratracheal route under anesthesia (200 μL of a mixture of Ketamine/Xylazine).

Figure 11:
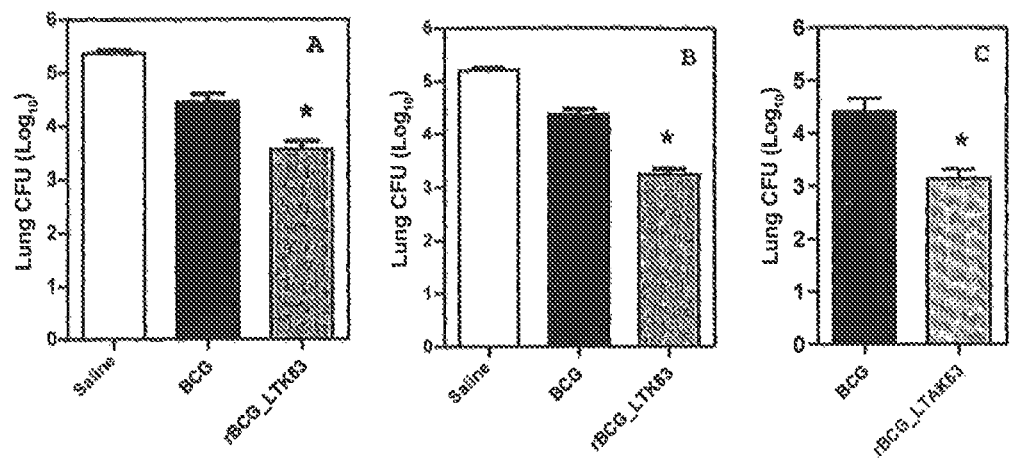
FIG. 11 shows the result of the protection assays involving intratracheal challenge with the *M. tuberculosis* H37Rv strain. Female BALB/c mice (n=10 per group) A and B were immunized subcutaneously with a single injection of *M. bovis* BCG or with rBCG-LT. A non-immunized group was used as negative control. Eight weeks after the immunization the animals were challenged by the intratracheal route with $1 \times 10^5$ CFU of *M. tuberculosis* H37Rv. Error bars represent the standard deviation of the mean. A and B represent two assays conducted at different times under the same conditions. C represents an assay conducted with female C57BL/6 mice (n=10 per group) immunized subcutaneously with a single injection of *M. bovis* BCG or rBCG-LTA. Eight weeks after the immunization the animals were challenged by the intratracheal route with $1 \times 10^5$ CFU of *M. tuberculosis* H37Rv. Error bars represent the standard deviation of the mean.

The animals were followed up for four weeks. After this period they were all sacrificed in a $CO_2$ chamber and their lungs were removed for processing. One of the lobules of each lung was separated and macerated in a total volume of 1 mL of PBS 1× solution. Then this material was serially diluted and seeded in petri dishes containing MB7H10/OADC solid medium. Thirty days later, the number of CFU was determined in the plates corresponding to each group of immunized animals (FIG. 11).

The invention claimed is:

1. A recombinant *Mycobacterium* strain that encodes a mutant *Escherichia coli* heat-labile toxin LT, or a mutant A subunit thereof, wherein the *Escherichia coli* heat-labile toxin LT is mutated at position 63 of SEQ ID NO: 11, and wherein the mutation is a substitution of serine for lysine.

2. The recombinant *Mycobacterium* strain according to claim 1, wherein the strain encodes the LTAK63 (SEQ ID NO: 8) subunit of the mutant *Escherichia coli* heat-labile toxin LT.

3. The recombinant *Mycobacterium* strain according to claim 1, wherein the *Escherichia coli* heat-labile toxin LT is that produced by SEQ ID NO: 1.

4. The recombinant *Mycobacterium* strain according to claim 2, wherein the LTAK63 is that of SEQ ID NO: 7.

5. The recombinant *Mycobacterium* strain according to claim 1, wherein the strain of recombinant *Mycobacterium* is selected from the group consisting of a strain of *Mycobacterium tuberculosis*, *Mycobacterium bovis* Bacillus Calmette Guerin (BCG), *Mycobacterium microtti*, *Mycobacterium africanum*, *Mycobacterium smegmatis*, *Mycobacterium avium*, and *Mycobacterium vaccae*.

6. The recombinant *Mycobacterium* strain according to claim 5, wherein the strain of recombinant *Mycobacterium* is a strain of *Mycobacterium bovis* Bacillus Calmette Guerin (BCG).

7. An immunogenic composition comprising the recombinant *Mycobacterium* strain of claim 1, and a physiologically acceptable vehicle, excipient, diluent, or solvent.

8. The immunogenic composition according to claim 7, further comprising one or more antigens, wherein the antigens are inactivated toxins.

9. The immunogenic composition according to claim 7, wherein said composition is formulated for intradermal, oral, or parenteral administration.

10. A method for preventing or treating diseases and/or treating infections caused by bacteria of the genus *Mycobacterium*, comprising administering to an animal in need thereof immunogenic composition of claim 7.

11. The method of claim 10, wherein the disease is tuberculosis.

12. The method according to claim 10, wherein the animal is a mammal.

13. The method according to claim 12, wherein the mammal is a human.

14. A method for preventing or treating diseases and/or treating infections caused by bacteria of the genus *Mycobacterium*, comprising administering to an animal in need thereof an effective amount of the recombinant *Mycobacterium* strain of claim 1.

15. The method of claim 14, wherein the disease is tuberculosis.

16. An immunogenic composition comprising the recombinant *Mycobacterium* strain of claim 2, and a physiologically acceptable vehicle, excipient, diluent, or solvent.

17. A method for preventing or treating diseases and/or treating infections caused by bacteria of the genus *Mycobacterium*, comprising administering to an animal in need thereof an effective amount of the immunogenic composition of claim 16.

18. The method of claim 17, wherein the disease is tuberculosis.

19. A method for preventing or treating diseases and/or treating infections caused by bacteria of the genus *Mycobacterium*, comprising administering to an animal in need thereof an effective amount of the recombinant *Mycobacterium* strain of claim 2.

20. The method of claim 19, wherein the disease is tuberculosis.

* * * * *

SEQUENCE LISTING

```
<160> NUMBER OF SEQ ID NOS: 11

<210> SEQ ID NO 1
<211> LENGTH: 7887
<212> TYPE: DNA
<213> ORGANISM: Artificial Sequence
<220> FEATURE:
<223> OTHER INFORMATION: Description of Artificial Sequence: Synthetic
      Gene sequence of plasmid pNP12-LTK63

<400> SEQUENCE: 1
gcgcccaata cgcaaaccgc ctctccccgc gcgttggccg attcattaat gcagctggca      60
cgacaggttt cccgactgga aagcgggcag tgagcgcaac gcaattaatg tgagttagct     120
cactcattag gcaccccagg ctttacactt tatgcttccg gctcgtatgt tgtgtggaat     180
tgtgagcgga taacaatttc acacaggaaa cagctatgac catgattacg aattcgagct     240
cgacttaatt aactccgggt ggtcactgag tacatcccgt cggtgcgttc ggcatcggtc     300
ggggtgtggg tgggtgtcgg ctcccgcgac gaaggacgaa gcgtcgcggg tgccgcccac     360
ttcttggagc atctgctgtt caaggccacc ccgacgcgca cgcggtcgac atcgcgcagg     420
ctgtcgatgc cgtcggcggt gagctgaacg cgttcaccac gcgcgagcac acctgttact     480
acgcgcatgt gctcgactcc gacctggagc tcgcggtcga cctggtgcgc cgatgtcgtg     540
ttgcgtgggc gttgtgccac cgaggatgtc gaagtggagc gcgacgtcgt cctcgaggag     600
atcgccatgc gtgacgacga tcccgaggac agcctcggcg acgtgttcct ctcggcgatg     660
```

```
ttcggcgatc acccggtggg acgtccggtg atcggcagcg tcgagtcgat cgagaccatg      720
acgcgtgcac agctgcattc gttccacgtc cggcgttaca cacccgaacg gatgatcgtg      780
gcggtggccg gcaacgtcga ccacgacgtg tggtgtcgtt ggtccgagag catttcggcc      840
cccggctgga ggccgacgtt ccgcggtggc tccccgtaag gctcgggacg ggtcggtggt      900
aagccatcgc tgctcgtggt cgaccgcgac ggggaacagt cccatgtctc gctgggcgtt      960
cgcacgcccg gccggcactg ggagcaccgg tgggccctgt cggtgttgaa caccgcgctg     1020
ggaggcgggc tcagttctcg tctgttccaa cagattcgcg agtcccgcgg cctggcctac     1080
ctcggtgtac tcgaccgtgg accacttcgc gacagcgggg ctctgtcggt gtatgcggga     1140
tgtcagccgg aacgtttcga cgaagtggtg cgggtgacca ccgaagtttt ggaaggtgtt     1200
gccagagacg ggatcaccgc cgacgaatgc cggatcgcca aggctcgtt gcgcggtggg      1260
ctggtgctcg gcctggagga ttccggatca cgtatgcacc ggatcggccg tagcgagctc     1320
aattacggtg gagcaccgga ccatcgacca cacgctggcc cagatcgagg cagtcactct     1380
agaagaggtc aacgccgtcg ctcaccagtt gctgtcgcgg gactacggtg ccgccgtact     1440
cggtccctat agttcgaaaa aggcgctgcc acaacagctt caaactatcg ccggctgacc     1500
cgctacactg gtccaatgg attagaagga gaagtaccga tgggatccgg taccaatggc      1560
gacagattat accgtgctga ctctagaccc ccagatgaaa taaaacgttc cggaggtctt     1620
atgcccagag gcataatga gtacttcgat agaggaactc aaatgaatat taatctttat      1680
gatcacgcga gaggaacaca aaccggcttt gtcagatatg atgacggata tgtttccact     1740
aagcttagtt tgagaagtgc tcacttagca ggacagtcta tattatcagg atattccact     1800
tactatatat atgttatagc gacagcacca aatatgttta atgttaatga tgtattaggc     1860
gtatacagcc ctcacccata tgaacaggag gtttctgcgt taggtggaat accatattct     1920
cagatatatg gatggtatcg tgttaatttt ggtgtgattg atgaacgatt acatcgtaac     1980
agggaatata gagaccggta ttacagaaat ctgaatatag ctccggcaga ggatggttac     2040
agattagcag gtttcccacc ggatcaccaa gcttggagag aagaaccctg gattcatcat     2100
gcaccacaag gttgtggaaa ttcatcaaga acaatcacag gtgatacttg taatgaggag     2160
acccagaatc tgagcacaat atatctcagg gaatatcaat caaaagttaa gaggcagata     2220
ttttcagact atcagtcaga ggttgacata taacagaa ttcgggatga attatgagga       2280
ttaggagaag taccggaatt catgaataaa gtaaaatgtt atgtttat tacggcgtta      2340
ctatcctctc tatgtgcata cggagctccc cagtctatta cagaactatg ttcggaatat     2400
cgcaacacac aaatatatac gataaatgac aagatactat catatacgga atcgatggca     2460
ggcaaaagag aaatggttat cattacattt aagagcggcg caacatttca ggtcgaagtc     2520
ccgggcagtc aacatataga ctcccaaaaa aaagccattg aaaggatgaa ggacacatta     2580
agaatcacat atctgaccga gaccaaaatt gataaattat gtgtatggaa taataaaacc     2640
cccaattcaa ttgcggcaat cagtatggaa aactagctgc agcatcacca tcaccatcac     2700
tagtgaaata gcgaaacacg ggatcgggcg agttcgacct tccgtcggtc tcgccctatt     2760
aatagtggca tgcaagcttg gcactggccg tcgttttaca acgtcgtgac tgggaaaacc     2820
ctggcgttac ccaacttaat cgccttgcag cacatccccc tttcgccagc tggcgtaata     2880
gcgaagaggc ccgcaccgat cgcccttccc aacagttgcg cagcctgaat ggcgaatggc     2940
gcctgatgcg gtattttctc cttacgcatc tgtgcggtat ttcacaccgc atatgcaggg     3000
gggggggggc gctgaggtct gcctcgtgaa gaaggtgttg ctgactcata ccaggaacga     3060
```

```
ggacagtcgc acgacgaagt tcttctggat cgcgcccgtg ctggaagcac tcaacctcga    3120
agcgtgtggt tgcggagcca tctagcaacc acacgaaaca tgcgcaacga accgcgcaac    3180
gaacaacgcc tagaactggc cctagatgag ctgactcgta tcgttggtaa acctagtttg    3240
accagcatgt tttaactacg ttcggtgagc tgtcaacggg gcctgtaacg gcacaacgaa    3300
ccgtgcaacg agagtggcca cggatgccac cacaggcact acaacggagt tcgccacgta    3360
catcaccaca accaccgatt ctggcggtga gctccccgat attcagcgga aatggcttgg    3420
tatcgaccaa gattcgtaga accccgtctc gtctggctgg tattcaaaac gggcgcaacg    3480
aaacacgcaa cgagacaggc atgcccaaa ccagaaaact agcgtctacc aggactttta    3540
cctgtccgac ccgttgcaac ggaaccccca cggaaccccc gcgacacccc gctccccaat    3600
tgcgttagaa cagcggtgga ttgtcggctt cgttgtgggc cttttgagcc gcttcctgtt    3660
ctgccgcacg ctctttcctc gcccgatagc cgagtcgctt aacggtgtcc agatgcagcc    3720
cgaaatgttt ggccgtttgc ggccaagagt ggccctcgtc gtcgtgatag gcgcggatgc    3780
gttcgcggcg tgcagcctgc tcggcgagcc actcgctgcg ttcctgcgcc acgagccgga    3840
cgacgtggcg ttcggatagt ccggtgattc gagcgccttc ggcggcggtc acgcgccgct    3900
ttttgcggac agtcggctgc cggttgtagc cgtcgctgta gccgtcgctc atagcaatgc    3960
ctccatggct gacgcggact ttgcgcgccg cgcaactgtg ctcgccgccg tgcgcgctgc    4020
tgcgcccttc gcgagatgg ccgactggcg cgcactgagt gtggcctcgt agaccacgat    4080
cccgtccgcc caaatgcgcg acttggttgt gatccaacgc caaatgctgt ggcgatggc    4140 gcggacctcg ctgtccggta gcggtccggg acacacgtcg ttgcacggga attcggcgtt    4200
tcgcgcgtgg cactcggcat agatcgcgcg gccgagtccg tccacgttcc gggtcggcag    4260
gtagatccgc atgagggcgg gacgataggc ccacaacctg acggaatcga acagtgcgca    4320
attccgccct agcggcgtcg gagccgcttt gtacgtggtc tgctgacgcc agcgcggcgg    4380
tggcatgttc gcgccgagct cggcctcgat gtggctgagt gtgtagagat ctgagtggag    4440
ccattccgtt tcccaggcga tgtggccggg gttttggtc atgaggcctg agtaactgcg    4500
gtcgccgtcg acgcgcgcc gaaggccttc ggcgcacgcc gccatgtatg cgagcggctt    4560
acgccgcgcg tattcggtgc gtggaacagg ggcgttgagt gcccacactg cgtgtgcgtg    4620
gccgttggcg cgattgccca cgatcgcgtt gggcagcgga tggacccccc gggcgctgag    4680
cgctcggagc gctgcgtctg gatggtctac gtccacgacc agcaggtttg ccagcgctgt    4740
tgggttcgcc tcgatgtacc ggcggcctag ggccgacgcg cggctttggc ggtagatccc    4800
ctcgagcaga tcgtcgcttg ccagcggcca gtacggcagc cagagctgct caaattcgtc    4860
ggcgacgtgc tcacgcttg gtagtagacc acgattaatc accggtgtat ggtccgacac    4920
gagctccaag tcagatattt cgctgagggg ccaccccaca actgcacact cccccgctct    4980
cccgtcgagc cctggtggtg aacaccagc gacagccgag cacccccaac cacctgtacc    5040
aaccaggagg aacacatgcg tcgtttcgag gacgtttccg ggccgctgag agccgctgtg    5100
gcggccgtac acgccgcctt agacccgtta gaccccctgc cgcctgaatg cgcgggtacg    5160
agccacacag cgcccgaact tacgagctg gtgggctcac ctggctttat ggcgtacgaa    5220
tcggctgtgt gcgacctgtt gggcgaggtg aggtacgcgc tactcacgct ggcaagggcg    5280
acacagccgc cccaccgagc ccgcacggcc gcgcgcggtg tcaacaaccg ggtgagtcgt    5340
gcacaccagc aggtgttcga ggcttggctc gaagtgcagg acatcgtggc gaacgccgcc    5400
```

```
cgatgagccg cgccttacgc tggctgccag ccgttcgcgg gctggttggt gcagcgcgtc      5460
gagcggttag aggccctgcg gtgttccacc accgcagggc ctcgcccttt ttaaggctga      5520
atttgcttgt ctccgaatcc aactggcttg tccaagggtg tatctacgct taatccaaag     5580
ttcaaacgag gggattacac atgaccaact tcgataacgt tctcggctcg atcctgaatc     5640
gccccatcat ccagccagaa agtgagggag ccacggttga tgagagcttt gttgtaggtg     5700
gaccagttgg tgattttgaa cttttgcttt gccacggaac ggtctgcgtt gtcgggaaga     5760
tgcgtgatct gatccttcaa ctcagcaaaa gttcgattta ttcaacaaag ccgccgtccc     5820
gtcaagtcag cgtaatgctc tgccagtgtt acaaccaatt aaccaattct gattagaaaa     5880
actcatcgag catcaaatga aactgcaatt tattcatatc aggattatca ataccatatt     5940
tttgaaaaag ccgtttctgt aatgaaggag aaaactcacc gaggcagttc cataggatgg     6000
caagatcctg gtatcggtct gcgattccga ctcgtccaac atcaatacaa cctattaatt     6060
tcccctcgtc aaaataagg ttatcaagtg agaaatcacc atgagtgacg actgaatccg      6120
gtgagaatgg caaaagctta tgcatttctt tccagacttg ttcaacaggc cagccattac     6180
gctcgtcatc aaaatcactc gcatcaacca accgttatt cattcgtgat tgcgcctgag      6240
cgagacgaaa tacgcgatcg ctgttaaaag gacaattaca acaggaatc gaatgcaacc      6300 ggcgcaggaa cactgccagc gcatcaacaa tattttcacc tgaatcagga tattcttcta     6360
atacctggaa tgctgttttc ccggggatcg cagtggtgag taaccatgca tcatcaggag     6420
tacggataaa atgcttgatg gtcggaagag gcataaattc cgtcagccag tttagtctga     6480
ccatctcatc tgtaacatca ttggcaacgc tacctttgcc atgtttcaga aacaactctg     6540
gcgcatcggg cttcccatac aatcgataga ttgtcgcacc tgattgcccg acattatcgc     6600
gagcccattt atacccatat aaatcagcat ccatgttgga atttaatcgc ggcctcgagc     6660
aagacgtttc ccgttgaata tggctcataa caccccttgt attactgttt atgtaagcag     6720
acagttttat tgttcatgat gatatatttt tatcttgtgc aatgtaacat cagagatttt     6780
gagacacaac gtggctttcc cccccccccc tatcattgca gcactgggc cagatggtaa       6840 gccctcccgt atcgtagtta tctacacgac ggggagtcag gcaactatgg atgaacgaaa     6900
tagacagatc gctgagatag gtgcctcact gattaagcat tggtaactgt cagaccaagt     6960
ttactcatat atactttaga ttgatttaaa acttcatttt taatttaaaa ggatctaggt     7020
gaagatcctt tttgataatc tcatgaccaa aatcccttaa cgtgagtttt cgttccactg     7080
agcgtcagac cccgtagaaa agatcaaagg atcttcttga gatcctttt ttctgcgcgt      7140 aatctgctgc ttgcaaacaa aaaaaccacc gctaccagcg gtggtttgtt tgccggatca     7200
agagctacca actcttttc cgaaggtaac tggcttcagc agagcgcaga taccaaatac      7260
tgtccttcta gtgtagccgt agttaggcca ccacttcaag aactctgtag caccgcctac     7320
atacctcgct ctgctaatcc tgttaccagt ggctgctgcc agtggcgata agtcgtgtct     7380
taccgggttg gactcaagac gatagttacc ggataaggcg cagcggtcgg gctgaacggg     7440
gggttcgtgc acacagccca gcttggagcg aacgacctac accgaactga gatacctaca     7500
gcgtgagcta tgagaaagcg ccacgcttcc cgaagggaga aaggcggaca ggtatccggt     7560
aagcggcagg gtcggaacag gagagcgcac gagggagctt ccagggggaa acgcctggta     7620
tctttatagt cctgtcgggt ttcgccacct ctgacttgag cgtcgatttt tgtgatgctc     7680
gtcagggggg cggagcctat ggaaaaacgc cagcaacgcg gccttttac ggttcctggc      7740 cttttgctgg ccttttgctc acatgttctt tcctgcgtta tcccctgatt ctgtggataa     7800
```

```
ccgtattacc gcctttgagt gagctgatac cgctcgccgc agccgaacga ccgagcgcag      7860
cgagtcagtg agcgaggaag cggaaga                                          7887

<210> SEQ ID NO 2
<211> LENGTH: 7488
<212> TYPE: DNA
<213> ORGANISM: Artificial Sequence
<220> FEATURE:
<223> OTHER INFORMATION: Description of Artificial Sequence: Synthetic
      Gene sequence of plasmid pNL12-LTAK63

<400> SEQUENCE: 2
gcgcccaata cgcaaaccgc ctctcccgc gcgttggccg attcattaat gcagctggca         60
cgacaggttt cccgactgga aagcgggcag tgagcgcaac gcaattaatg tgagttagct       120
cactcattag gcaccccagg ctttacactt tatgcttccg gctcgtatgt tgtgtggaat       180
tgtgagcgga taacaatttc acacaggaaa cagctatgac catgattacg aattcgagct       240
cgacttaatt aactccgggt ggtcactgag tacatcccgt cggtgcgttc ggcatcggtc       300
ggggtgtggg tggtgtcgg ctcccgcgac gaaggacgaa gcgtcgcggg tgccgcccac       360
ttcttggagc atctgctgtt caaggccacc ccgacgcgca cgcggtcgac atcgcgcagg       420
ctgtcgatgc cgtcggcggt gagctgaacg cgttcaccac gcgcgagcac acctgttact       480
acgcgcatgt gctcgactcc gacctggagc tcgcggtcga cctggtgcgc cgatgtcgtg       540
ttgcgtgggc gttgtgccac cgaggatgtc gaagtggagc gcgacgtcgt cctcgaggag       600
atcgccatgc gtgacgacga tcccgaggac agcctcggcg acgtgttcct ctcggcgatg       660
ttcggcgatc acccggtggg acgtccggtg atcggcagcg tcgagtcgat cgagaccatg       720
acgcgtgcac agctgcattc gttccacgtc cggcgttaca cacccgaacg gatgatcgtg       780
gcggtggccg gcaacgtcga ccacgacgtg tggtgtcgtt ggtccgagag catttcggcc       840
cccggctgga ggccgacgtt ccgcggtggc tccccgtaag gctcgggacg ggtcggtggt       900
aagccatcgc tgctcgtggt cgaccgcgac ggggaacagt cccatgtctc gctgggcgtt       960
cgcacgcccg gccggcactg ggagcaccgg tgggccctgt cggtgttgaa caccgcgctg      1020
ggaggcgggc tcagttctcg tctgttccaa cagattcgcg agtcccgcgg cctggcctac      1080
ctcggtgtac tcgaccgtgg accacttcgc gacagcgggg ctctgtcggt gtatgcggga      1140
tgtcagccgg aacgtttcga cgaagtggtg cgggtgacca ccgaagtttt ggaaggtgtt      1200
gccagagacg ggatcaccgc cgacgaatgc cggatcgcca aggctcgtt gcgcggtggg       1260 ctggtgctcg gcctggagga ttccggatca cgtatgcacc ggatcggccg tagcgagctc      1320
aattacggtg gagcaccgga ccatcgacca cacgctggcc cagatcgagg cagtcactct      1380
agaagaggtc aacgccgtcg ctcaccagtt gctgtcgcgg gactacggtg ccgccgtact      1440
cggtccctat agttcgaaaa aggcgctgcc acaacagctt caaactatcg ccggctgacc      1500
cgctacactg gtccaatgg attagaagga gaagtaccga tgggatccgg taccaatggc       1560
gacagattat accgtgctga ctctagaccc ccagatgaaa taaaacgttc cggaggtctt      1620
atgcccagag gcataatga gtacttcgat agaggaactc aaatgaatat taatctttat      1680
gatcacgcga gaggaacaca aaccggcttt gtcagatatg atgacggata tgtttccact      1740
aagcttagtt tgagaagtgc tcacttagca ggacagtcta tattatcagg atattccact      1800
tactatatat atgttatagc gacagcacca aatatgttta atgttaatga tgtattaggc      1860
gtatacagcc ctcacccata tgaacaggag gtttctgcgt taggtggaat accatattct      1920
```

```
cagatatatg gatggtatcg tgttaatttt ggtgtgattg atgaacgatt acatcgtaac    1980
agggaatata gagaccggta ttacagaaat ctgaatatag ctccggcaga ggatggttac    2040
agattagcag gtttcccacc ggatcaccaa gcttggagag aagaaccctg gattcatcat    2100
gcaccacaag gttgtggaaa ttcatcaaga acaatcacag tgatacttg  taatgaggag    2160 acccagaatc tgagcacaat atatctcagg gaatatcaat caaaagttaa gaggcagata    2220
ttttcagact atcagtcaga ggttgacata taacagaa   ttcgggatga attatgactg    2280
cagcatcacc atcaccatca ctagtgaaat agcgaaacac gggatcgggc gagttcgacc    2340
ttccgtcggt ctcgccctat taatagtggc atgcaagctt ggcactggcc gtcgttttac    2400
aacgtcgtga ctgggaaaac cctggcgtta cccaacttaa tcgccttgca gcacatcccc    2460
ctttcgccag ctggcgtaat agcgaagagg cccgcaccga tcgcccttcc caacagttgc    2520
gcagcctgaa tggcgaatgg cgcctgatgc ggtattttct ccttacgcat ctgtgcggta    2580
tttcacaccg catatgcagg gggggggggg cgctgaggtc tgcctcgtga agaaggtgtt    2640
gctgactcat accaggaacg aggacagtcg cacgacgaag ttcttctgga tcgcgcccgt    2700
gctggaagca ctcaacctcg aagcgtgtgg ttgcggagcc atctagcaac cacacgaaac    2760
atgcgcaacg aaccgcgcaa cgaacaacgc ctagaactgg ccctagatga gctgactcgt    2820
atcgttggta aacctagttt gaccagcatg ttttaactac gttcggtgag ctgtcaacgg    2880
ggcctgtaac ggcacaacga accgtgcaac gagagtggcc acggatgcca ccacaggcac    2940
tacaacggag ttcgccacgt acatcaccac aaccaccgat tctggcggtg agctccccga    3000
tattcagcgg aaatggcttg gtatcgacca agattcgtag aaccccgtct cgtctggctg    3060
gtattcaaaa cgggcgcaac gaaacacgca acgagacagg catggcccaa accagaaaac    3120
tagcgtctac caggactttt acctgtccga cccgttgcaa cggaaccccc cacggaaccc    3180
ccgcgacacc cgctccccaa ttgcgttaga acagcgtgg  attgtcggct tcgttgtggg    3240 cctttttgagc cgcttcctgt tctgccgcac gctctttcct cgcccgatag ccgagtcgct    3300
taacggtgtc cagatgcagc ccgaaatgtt tggccgtttg cggccaagag tggccctcgt    3360
cgtcgtgata ggcgcggatg cgttcgcggc gtgcagcctg ctcggcgagc cactcgctgc    3420
gttcctgcgc cacgagccgg acgacgtggc gttcggatag tccggtgatt cgagcgcctt    3480
cggcggcggt cacgcgccgc tttttgcgga cagtcggctg ccggttgtag ccgtcgctgt    3540
agccgtcgct catagcaatg cctccatggc tgacgcggac tttgcgcgcc gcgcaactgt    3600
gctcgccgcc gtgcgcgctg ctgcgccctt ccgcgagatg gccgactggc gcgcactgag    3660
tgtggcctcg tagaccacga tcccgtccgc ccaaatgcgc gacttggttg tgatccaacg    3720
ccaaatgctg ttggcgatgg cgcggacctc gctgtccggt agcggtccgg gacacacgtc    3780
gttgcacggg aattcggcgt ttcgcgcgtg gcactcggca tagatcgcgc ggccgagtcc    3840
gtccacgttc cgggtcggca ggtagatccg catgagggcg ggacgatagg cccacaacct    3900
gacggaatcg aacagtgcgc aattccgccc tagcggcgtc ggagccgctt tgtacgtggt    3960
ctgctgacgc cagcgcggcg gtggcatgtt cgcgccgagc tcggcctcga tgtggctgag    4020
tgtgtagaga tctgagtgga gccattccgt ttcccaggcg atgtgccgg  ggttttggt    4080 catgaggcct gagtaactgc ggtcgccgtc gacggcgcgc cgaaggcctt cggcgcacgc    4140
cgccatgtat gcgagcggct tacgccgcgc gtattcggtg cgtggaacag gggcgttgag    4200
tgcccacact gcgtgtgcgt ggccgttggc gcgattgccc acgatcgcgt tgggcagcgg    4260
```

-continued

```
atgggacccc cgggcgctga gcgctcggag cgctgcgtct ggatggtcta cgtccacgac   4320
cagcaggttt gccagcgctg ttgggttcgc ctcgatgtac cggcggccta gggccgacgc   4380
gcggctttgg cggtagatcc cctcgagcag atcgtcgctt gccagcggcc agtacggcag   4440
ccagagctgc tcaaattcgt cggcgacgtg gctcacgctt ggtagtagac cacgattaat   4500
caccggtgta tggtccgaca cgagctccaa gtcagatatt tcgctgaggg gccacccac    4560 aactgcacac tcccccgctc tcccgtcgag ccctggtggt ggaacaccag cgacagccga   4620 gcaccccccaa ccacctgtac caaccaggag gaacacatgc gtcgtttcga ggacgtttcc   4680
gggccgctga gagccgctgt ggcggccgta cacgccgcct tagacccgtt agacccctg    4740 ccgcctgaat gcgcgggtac gagccacaca gcgcccgaac ttacggagct ggtgggctca   4800
cctggcttta tggcgtacga atcgctgtg tgcgacctgt tgggcgaggt gaggtacgcg    4860
ctactcacgc tggcaagggc gacacagccg ccccaccgag cccgcacggc cgcgcgcggt   4920
gtcaacaacc gggtgagtcg tgcacaccag caggtgttcg aggcttggct cgaagtgcag   4980
gacatcgtgg cgaacgccgc ccgatgagcc gcgccttacg ctggctgcca gccgttcgcg   5040
ggctggttgg tgcagcgcgt cgagcggtta gaggccctgc ggtgttccac caccgcaggg   5100
cctcgccctt tttaaggctg aatttgcttg tctccgaatc caactggctt gtccaagggt   5160
gtatctacgc ttaatccaaa gttcaaacga ggggattaca catgaccaac ttcgataacg   5220
ttctcggctc gatcctgaat cgccccatca tccagccaga aagtgaggga gccacgttg    5280 atgagagctt tgttgtaggt ggaccagttg gtgattttga acttttgctt tgccacggaa   5340
cggtctgcgt tgtcgggaag atgcgtgatc tgatccttca actcagcaaa agttcgattt   5400
attcaacaaa gccgccgtcc cgtcaagtca gcgtaatgct ctgccagtgt acaaccaat    5460 taaccaattc tgattagaaa aactcatcga gcatcaaatg aaactgcaat ttattcatat   5520
caggattatc aataccatat ttttgaaaaa gccgtttctg taatgaagga gaaaactcac   5580
cgaggcagtt ccataggatg gcaagatcct ggtatcggtc tgcgattccg actcgtccaa   5640
catcaataca acctattaat ttcccctcgt caaaaataag gttatcaagt gagaaatcac   5700
catgagtgac gactgaatcc ggtgagaatg gcaaaagctt atgcatttct ttccagactt   5760
gttcaacagg ccagccatta cgctcgtcat caaaatcact cgcatcaacc aaaccgttat   5820
tcattcgtga ttgcgcctga gcgagacgaa atacgcgatc gctgttaaaa ggacaattac   5880
aaacaggaat cgaatgcaac cggcgcagga acactgccag cgcatcaaca atattttcac   5940
ctgaatcagg atattcttct aatacctgga atgctgtttt cccggggatc gcagtggtga   6000
gtaaccatgc atcatcagga gtacggataa aatgcttgat ggtcggaaga ggcataaatt   6060
ccgtcagcca gtttagtctg accatctcat ctgtaacatc attggcaacg ctacctttgc   6120
catgtttcag aaacaactct ggcgcatcgg gcttcccata caatcgatag attgtcgcac   6180
ctgattgccc gacattatcg cgagcccatt tatacccata taaatcagca tccatgttgg   6240
aatttaatcg cggcctcgag caagacgttt cccgttgaat atggctcata caccccttg    6300 tattactgtt tatgtaagca gacagttttta ttgttcatga tgatatattt ttatcttgtg   6360
caatgtaaca tcagagattt tgagacacaa cgtggctttc cccccccccc ctatcattgc   6420
agcactgggg ccagatggta agccctcccg tatcgtagtt atctacacga cggggagtca   6480
ggcaactatg gatgaacgaa atagacagat cgctgagata ggtgcctcac tgattaagca   6540
ttggtaactg tcagaccaag tttactcata tatactttag attgatttaa aacttcattt   6600
ttaatttaaa aggatctagg tgaagatcct ttttgataat ctcatgacca aaatccctta   6660
```

```
acgtgagttt tcgttccact gagcgtcaga ccccgtagaa aagatcaaag gatcttcttg    6720
agatcctttt tttctgcgcg taatctgctg cttgcaaaca aaaaaaccac cgctaccagc    6780
ggtggtttgt ttgccggatc aagagctacc aactctttt  ccgaaggtaa ctggcttcag    6840
cagagcgcag ataccaaata ctgtccttct agtgtagccg tagttaggcc accacttcaa    6900
gaactctgta gcaccgccta catacctcgc tctgctaatc ctgttaccag tggctgctgc    6960
cagtggcgat aagtcgtgtc ttaccgggtt ggactcaaga cgatagttac cggataaggc    7020
gcagcggtcg ggctgaacgg ggggttcgtg cacacagccc agcttggagc gaacgaccta    7080
caccgaactg agatacctac agcgtgagct atgagaaagc gccacgcttc ccgaagggag    7140
aaaggcggac aggtatccgg taagcggcag ggtcggaaca ggagagcgca cgagggagct    7200
tccaggggga aacgcctggt atctttatag tcctgtcggg tttcgccacc tctgacttga    7260
gcgtcgattt ttgtgatgct cgtcaggggg cggagccta  tggaaaaacg ccagcaacgc    7320
ggccttttta cggttcctgg ccttttgctg ccttttgct  cacatgttct ttcctgcgtt    7380
atcccctgat tctgtggata accgtattac cgcctttgag tgagctgata ccgctcgccg    7440
cagccgaacg accgagcgca gcgagtcagt gagcgaggaa gcggaaga                 7488

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tagggtaccc aaaatataa cttcattttt tttatttt                              38

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tagctgcagc tagttttca tactgattgc cc                                    32

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tagggatcca atggcgacag attataccgt tg                                   32

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 6
tagggtacct aattcatccc gaattctgtt ata                                    33

<210> SEQ ID NO 7
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Ser Gly Thr Asn Gly Asp Arg Leu Tyr Arg Ala Asp Ser Arg
1               5                   10                  15

Pro Pro Asp Glu Ile Lys Arg Ser Gly Gly Leu Met Pro Arg Gly His
            20                  25                  30

Asn Glu Tyr Phe Asp Arg Gly Thr Gln Met Asn Ile Asn Leu Tyr Asp
        35                  40                  45

His Ala Arg Gly Thr Gln Thr Gly Phe Val Arg Tyr Asp Asp Gly Tyr
    50                  55                  60

Val Ser Thr Lys Leu Ser Leu Arg Ser Ala His Leu Ala Gly Gln Ser
65                  70                  75                  80

Ile Leu Ser Gly Tyr Ser Thr Tyr Tyr Ile Tyr Val Ile Ala Thr Ala
                85                  90                  95

Pro Asn Met Phe Asn Val Asn Asp Val Leu Gly Val Tyr Ser Pro His
            100                 105                 110

Pro Tyr Glu Gln Glu Val Ser Ala Leu Gly Gly Ile Pro Tyr Ser Gln
        115                 120                 125

Ile Tyr Gly Trp Tyr Arg Val Asn Phe Gly Val Ile Asp Glu Arg Leu
    130                 135                 140

His Arg Asn Arg Glu Tyr Arg Asp Arg Tyr Arg Asn Leu Asn Ile
145                 150                 155                 160

Ala Pro Ala Glu Asp Gly Tyr Arg Leu Ala Gly Phe Pro Pro Asp His
                165                 170                 175

Gln Ala Trp Arg Glu Pro Trp Ile His His Ala Pro Gln Gly Cys
            180                 185                 190

Gly Asn Ser Ser Arg Thr Ile Thr Gly Asp Thr Cys Asn Glu Glu Thr
        195                 200                 205

Gln Asn Leu Ser Thr Ile Tyr Leu Arg Glu Tyr Gln Ser Lys Val Lys
    210                 215                 220

Arg Gln Ile Phe Ser Asp Tyr Gln Ser Glu Val Asp Ile Tyr Asn Arg
225                 230                 235                 240

Ile Arg Asp Glu Leu
                245

<210> SEQ ID NO 8
<211> LENGTH: 258
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Lys Asn Ile Thr Phe Ile Phe Phe Ile Leu Leu Ala Ser Pro Leu
1               5                   10                  15

Tyr Ala Asn Gly Asp Arg Leu Tyr Arg Ala Asp Ser Arg Pro Pro Asp

```
                    20                  25                  30
Glu Ile Lys Arg Ser Gly Gly Leu Met Pro Arg Gly His Asn Glu Tyr
                35                  40                  45

Phe Asp Arg Gly Thr Gln Met Asn Ile Asn Leu Tyr Asp His Lys Arg
 50                  55                  60

Gly Thr Gln Thr Gly Phe Val Arg Tyr Asp Asp Gly Tyr Val Ser Thr
 65                  70                  75                  80

Ser Leu Ser Leu Arg Ser Ala His Leu Ala Gly Gln Ser Ile Leu Ser
                 85                  90                  95

Gly Tyr Ser Thr Tyr Tyr Ile Tyr Val Ile Ala Thr Ala Pro Asn Met
                100                 105                 110

Phe Asn Val Asn Asp Val Leu Gly Val Tyr Ser Pro His Pro Tyr Glu
                115                 120                 125

Gln Glu Val Ser Ala Leu Gly Gly Ile Pro Tyr Ser Gln Ile Tyr Gly
                130                 135                 140

Trp Tyr Arg Val Asn Phe Gly Val Ile Asp Glu Arg Leu His Arg Asn
145                 150                 155                 160

Arg Glu Tyr Arg Asp Arg Tyr Tyr Arg Asn Leu Asn Ile Ala Pro Ala
                165                 170                 175

Glu Asp Gly Tyr Arg Leu Ala Gly Phe Pro Asp His Gln Ala Trp
                180                 185                 190

Arg Glu Glu Pro Trp Ile His His Ala Pro Gln Gly Cys Gly Asn Ser
                195                 200                 205

Ser Arg Thr Ile Thr Gly Asp Thr Cys Asn Glu Glu Thr Gln Asn Leu
                210                 215                 220

Ser Thr Ile Tyr Leu Arg Glu Tyr Gln Ser Lys Val Lys Arg Gln Ile
225                 230                 235                 240

Phe Ser Asp Tyr Gln Ser Glu Val Asp Ile Tyr Asn Arg Ile Arg Asp
                245                 250                 255

Glu Leu

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asn Lys Val Lys Cys Tyr Val Leu Phe Thr Ala Leu Leu Ser Ser
 1               5                  10                  15

Leu Cys Ala Tyr Gly Ala Pro Gln Ser Ile Thr Glu Leu Cys Ser Glu
                20                  25                  30

Tyr Arg Asn Thr Gln Ile Tyr Thr Ile Asn Asp Lys Ile Leu Ser Tyr
                35                  40                  45

Thr Glu Ser Met Ala Gly Lys Arg Glu Met Val Ile Ile Thr Phe Lys
                50                  55                  60

Ser Gly Ala Thr Phe Gln Val Glu Val Pro Gly Ser Gln His Ile Asp
 65                  70                  75                  80

Ser Gln Lys Lys Ala Ile Glu Arg Met Lys Asp Thr Leu Arg Ile Thr
                 85                  90                  95

Tyr Leu Thr Glu Thr Lys Ile Asp Lys Leu Cys Val Trp Asn Asn Lys
                100                 105                 110

Thr Pro Asn Ser Ile Ala Ala Ile Ser Met Glu Asn
```

115                 120

<210> SEQ ID NO 10
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gly Ser Gly Thr Asn Gly Asp Arg Leu Tyr Arg Ala Asp Ser Arg
1               5                   10                  15

Pro Pro Asp Glu Ile Lys Arg Ser Gly Gly Leu Met Pro Arg Gly His
            20                  25                  30

Asn Glu Tyr Phe Asp Arg Gly Thr Gln Met Asn Ile Asn Leu Tyr Asp
        35                  40                  45

His Ala Arg Gly Thr Gln Thr Gly Phe Val Arg Tyr Asp Asp Gly Tyr
    50                  55                  60

Val Ser Thr Lys Leu Ser Leu Arg Ser Ala His Leu Ala Gly Gln Ser
65                  70                  75                  80

Ile Leu Ser Gly Tyr Ser Thr Tyr Tyr Ile Tyr Val Ile Ala Thr Ala
                85                  90                  95

Pro Asn Met Phe Asn Val Asn Asp Val Leu Gly Val Tyr Ser Pro His
            100                 105                 110

Pro Tyr Glu Gln Glu Val Ser Ala Leu Gly Gly Ile Pro Tyr Ser Gln
        115                 120                 125

Ile Tyr Gly Trp Tyr Arg Val Asn Phe Gly Val Ile Asp Glu Arg Leu
    130                 135                 140

His Arg Asn Arg Glu Tyr Arg Asp Arg Tyr Tyr Arg Asn Leu Asn Ile
145                 150                 155                 160

Ala Pro Ala Glu Asp Gly Tyr Arg Leu Ala Gly Phe Pro Pro Asp His
                165                 170                 175

Gln Ala Trp Arg Glu Glu Pro Trp Ile His His Ala Pro Gln Gly Cys
            180                 185                 190

Gly Asn Ser Ser Arg Thr Ile Thr Gly Asp Thr Cys Asn Glu Glu Thr
        195                 200                 205

Gln Asn Leu Ser Thr Ile Tyr Leu Arg Glu Tyr Gln Ser Lys Val Lys
    210                 215                 220

Arg Gln Ile Phe Ser Asp Tyr Gln Ser Glu Val Asp Ile Tyr Asn Arg
225                 230                 235                 240

Ile Arg Asp Glu Leu Met Asn Lys Val Lys Cys Tyr Val Leu Phe Thr
                245                 250                 255

Ala Leu Leu Ser Ser Leu Cys Ala Tyr Gly Ala Pro Gln Ser Ile Thr
            260                 265                 270

Glu Leu Cys Ser Glu Tyr Arg Asn Thr Gln Ile Tyr Thr Ile Asn Asp
        275                 280                 285

Lys Ile Leu Ser Tyr Thr Glu Ser Met Ala Gly Lys Arg Glu Met Val
    290                 295                 300

Ile Ile Thr Phe Lys Ser Gly Ala Thr Phe Gln Val Glu Val Pro Gly
305                 310                 315                 320

Ser Gln His Ile Asp Ser Gln Lys Lys Ala Ile Glu Arg Met Lys Asp
                325                 330                 335

Thr Leu Arg Ile Thr Tyr Leu Thr Glu Thr Lys Ile Asp Lys Leu Cys
            340                 345                 350

```
Val Trp Asn Asn Lys Thr Pro Asn Ser Ile Ala Ala Ile Ser Met Glu
        355                 360                 365
Asn

<210> SEQ ID NO 11
<211> LENGTH: 258
<212> TYPE: PRT
<213> ORGANISM: Escherichia coli

<400> SEQUENCE: 11

Met Lys Asn Ile Thr Phe Ile Phe Phe Ile Leu Leu Ala Ser Pro Leu
1               5                   10                  15

Tyr Ala Asn Gly Asp Arg Leu Tyr Arg Ala Asp Ser Arg Pro Pro Asp
            20                  25                  30

Glu Ile Lys Arg Ser Gly Gly Leu Met Pro Arg Gly His Asn Glu Tyr
        35                  40                  45

Phe Asp Arg Gly Thr Gln Met Asn Ile Asn Leu Tyr Asp His Ser Arg
    50                  55                  60

Gly Thr Gln Thr Gly Phe Val Arg Tyr Asp Asp Gly Tyr Val Ser Thr
65                  70                  75                  80

Ser Leu Ser Leu Arg Ser Ala His Leu Ala Gly Gln Ser Ile Leu Ser
                85                  90                  95

Gly Tyr Ser Thr Tyr Tyr Ile Tyr Val Ile Ala Thr Ala Pro Asn Met
            100                 105                 110

Phe Asn Val Asn Asp Val Leu Gly Val Tyr Ser Pro His Pro Tyr Glu
        115                 120                 125

Gln Glu Val Ser Ala Leu Gly Gly Ile Pro Tyr Ser Gln Ile Tyr Gly
    130                 135                 140

Trp Tyr Arg Val Asn Phe Gly Val Ile Asp Glu Arg Leu His Arg Asn
145                 150                 155                 160

Arg Glu Tyr Arg Asp Arg Tyr Tyr Arg Asn Leu Asn Ile Ala Pro Ala
                165                 170                 175

Glu Asp Gly Tyr Arg Leu Ala Gly Phe Pro Pro Asp His Gln Ala Trp
            180                 185                 190

Arg Glu Glu Pro Trp Ile His His Ala Pro Gln Gly Cys Gly Asn Ser
        195                 200                 205

Ser Arg Thr Ile Thr Gly Asp Thr Cys Asn Glu Glu Thr Gln Asn Leu
    210                 215                 220

Ser Thr Ile Tyr Leu Arg Glu Tyr Gln Ser Lys Val Lys Arg Gln Ile
225                 230                 235                 240

Phe Ser Asp Tyr Gln Ser Glu Val Asp Ile Tyr Asn Arg Ile Arg Asp
                245                 250                 255

Glu Leu
```